United States Patent [19]
Fujii et al.

[11] Patent Number: 5,652,710
[45] Date of Patent: Jul. 29, 1997

[54] SOLID/LIQUID DETERMINATION APPARATUS

[75] Inventors: Yuuko Fujii, Yamatokoriyama; Kenzo Ohji, Ikoma, both of Japan

[73] Assignee: Matsushita Electric Industrial Co., Ltd., Osaka, Japan

[21] Appl. No.: 348,004

[22] Filed: Dec. 1, 1994

[30] Foreign Application Priority Data

Dec. 10, 1993 [JP] Japan .................. 5-310392
Dec. 10, 1993 [JP] Japan .................. 5-319643

[51] Int. Cl.$^6$ ........................................ G01H 1/10
[52] U.S. Cl. ............... 364/508; 73/64.42; 73/64.53; 73/580; 73/662; 73/663
[58] Field of Search .................. 364/508; 73/64.42, 73/64.53, 457, 579, 580, 609, 618, 660, 662, 663

[56] References Cited

U.S. PATENT DOCUMENTS

| | | | |
|---|---|---|---|
| 3,435,664 | 4/1969 | Harris | 73/52 |
| 3,913,383 | 10/1975 | Kreula et al. | 73/52 |
| 4,393,088 | 7/1983 | Matsusaka | 426/234 |
| 4,595,827 | 6/1986 | Hirai et al. | 219/518 |
| 4,673,800 | 6/1987 | Hirai et al. | 219/518 |
| 4,703,151 | 10/1987 | Sakamoto | 219/518 |
| 4,875,533 | 10/1989 | Mihara et al. | 177/144 |
| 4,970,374 | 11/1990 | Ueda et al. | 219/518 |

FOREIGN PATENT DOCUMENTS

| | | |
|---|---|---|
| 0146406A2 | 6/1985 | European Pat. Off. |
| 2157522 | 6/1990 | Japan . |
| 4186145 | 7/1992 | Japan . |

*Primary Examiner*—Edward R. Cosimano
*Assistant Examiner*—Hien Vo
*Attorney, Agent, or Firm*—Panitch Schwarze Jacobs & Nadel, P.C.

[57] ABSTRACT

A turntable having a food of solid or liquid put in a container is rotated during a predetermined time period and then the rotation of the turntable is suspended. After the turntable is suspended, an amplitude of vibration of the turntable is detected by a vibration sensor, and when the amplitude of vibration is a predetermined value or more, the food is determined liquid, on the other hand, when the amplitude of vibration is smaller than the predetermined value, the food is determined to be solid.

12 Claims, 20 Drawing Sheets

SOLID/LIQUID DETERMINATION APPARATUS

BACKGROUND OF THE INVENTION AND RELATED ART STATEMENT

1. Field of the Invention

The present invention relates to a solid/liquid determination apparatus by which a state of an object, whether it is solid or liquid, is determined for the purpose of heating, and furthermore relates to an automatic oven comprising the solid/liquid determination apparatus.

2. Description of the Related Art

In a conventional automatic oven such as an electric oven or a microwave oven, for example, a weight of a food mounted in the oven is detected, and a heating time of the food is decided according to the detected weight. In another example of a conventional oven, steam emanated from the food is detected during heating operation, and when a predetermined amount of emanation of the steam is detected, the heating operation is completed. In such oven, the food is heated regardless of the state of the food whether the food is solid or liquid. As a result, a temperature or a finished state of the food is influenced by the state, solid or liquid, of the food.

In the apparatus in which the weight of the food is detected and the heating time is determined in accordance with the weight, even after microwave heating of the food of the same weight for the same length of time, the temperature of the finished state of boiled rice of a solid food is different from that of soup of a liquid food. FIG. 19 is a diagram representing a relation between heating time and temperature of the boiled rice or the soup. In this case, a heating object of 130 grams of the boiled rice or 130 grams of the soup is put in each cup of 70 grams of weight, and a cup of 200 grams filled with the boiled rice or the soup is heated in a microwave oven. Referring to FIG. 19, the heating time which is required to heat the object to about 77° C. (centigrade scale) is about 75 seconds in the case of the boiled rice as shown on a curve R, and the time is about 120 seconds in the case of the soup as shown on a curve MS. The soup requires as about 1.6 times long as the heating time of the boiled rice. The reason why the temperature rise of the soup is lower than that of the boiled rice is generally considered that the microwave concentrates on the surface of the soup or is reflected thereby due to the influences of a dielectric constant, an electric resistance, and/or an ionic conductivity by salt in the soup. It is considered that the such influences are small in the case of the boiled rice, and accordingly, the microwave penetrates into the boiled rice and a relatively large temperature rise is realized in comparison with the soup.

In general, a preferable temperature of the soup is about 77° C. and the preferable temperature of the boiled rice is about 90° C. Referring to FIG. 19, the heating times required to heat to the respective preferable temperatures are about 120 seconds for the soup as shown on the curve MS and about 90 seconds for the boiled rice as shown on the curve R. As mentioned above, speeds of temperature rises are different depending on the state of the food in the same weight, and thus the heating time for the boiled rice is different from the heating time of the soup to reach each optimum temperature.

Subsequently, the conventional automatic oven which is controlled by sensing steam emanated from a food by a steam sensor is described by taking the examples of the boiled rice and the soup. FIG. 20 is a diagram representing relation between the heating time and detected value of the steam sensor which detects the steam emanated from the boiled rice or the soup in heating operation. Small circles on curves R and MS represent heating times at the respective optimum temperatures. Referring to FIG. 20, the boiled rice emanates only small amount of steam as shown by the curve R. On the contrary, in the case of soup, an emanation of steam states immediately after a heating operation is started, and the emanation of steam greatly increases after about 85 seconds of heating time as shown by the curve MS. It is considered that the microwave concentrates on the surface of the soup, and the soup is heated in the vicinity of the surface. Consequently, the emanation of steam greatly increases. In the case of the boiled rice, the microwave penetrates into the boiled rice and diffuses therein, and consequently, the boiled rice is uniformly heated. Therefore, the emanation of the steam of the boiled rice lags behind that of the soup. For example, an output level of the steam sensor is about 0.12 volts when the boiled rice has been heated to the optimum temperature, and is about 0.58 volts when the soup has been heated to the optimum temperature. Therefore, control of the food temperature can not be realized by detecting the steam emanated from the food. Namely, in order to heat various foods to the respective preferable temperatures by the automatic oven, the heating time must be set according to the state of the food, whether it is solid or liquid. However, the above-mentioned conventional automatic ovens do not comprise really useful means for automatically determining the state of the food.

A method for detecting a solid-phase rate (it is considered to be a rate of solid state portion to liquid state portion in a melted alloy) of an alloy material in partly melted state is disclosed in the Japanese published unexamined patent application Hei 4-186145. According to the prior art, mechanical vibration is continuously applied to the alloy material in the melted state by an ultrasonic wave generator, and a variation of the vibration frequency is detected, keeping the application of the vibration to the alloy material. Then, the solid-phase rate is derived by experimental correspondence between the variation of the vibration frequency and the temperature change. The above-mentioned prior art requires a particular ultrasonic wave generator to give the mechanical vibration to the object to be measured, and such ultrasonic wave generator is expensive in cost. Furthermore, an ultrasonic sensor is generally delicate and is easily disturbed by various noises when applied to a microwave oven.

The solid/liquid determination apparatus of the present invention proposes a novel means for solving the problem in the prior art.

The inventor came to a novel concept that, without providing any particular sound or vibration generator, the difference of vibration corresponding to the states (solid or liquid) can be detected by measuring a vibration caused by stopping.

OBJECT AND SUMMARY OF THE INVENTION

An object of the present invention is to provide a solid/liquid determination apparatus for easily determining the state of a food such as solid or liquid without contacting the food.

Another object of the present invention is to provide an automatic oven comprising the solid/liquid determination apparatus of the present invention.

A solid/liquid determination apparatus in accordance with the present invention comprises:

a movable table for putting an object to be determined of state of solid or liquid, means for driving the table, control means for controlling driving of the movable table bearing the object to be determined, vibration detection means for detecting vibration of the table, and state determination means for determining the state of solid or liquid of the object by detecting the vibration of the movable table, by the vibration detection means, immediately after stop of the driving of the movable table so that the state of the object is liquid in the case that the amplitude of vibration is no less than a predetermined value and that the state of the object is solid in the case that the amplitude of vibration is smaller than the predetermined value.

An automatic oven comprising the solid/liquid determination apparatus comprises:

menu selecting means for selecting a kind of food to be heated, a heating chamber for mounting the food to be heated, heating means for heating the heating chamber, state determination means for determining state of the food to be solid or liquid, steam detection means for detecting steam emanated from the food, heating control means for controlling a heating time by the heating means on the basis of a predetermined heating constant corresponding to the food selected by the menu selecting means and determination result of the state determination means when a detected value of the steam detection means exceeds a predetermined level.

While the novel features of the invention are set forth particularly in the appended claims, the invention, both as to organization and content, will be better understood and appreciated, along with other objects and features thereof, from the following detailed description taken in conjunction with the drawings.

It will be recognized that some or all of the Figures are schematic representations for purposes of illustration and do not necessarily depict the actual relative sizes or locations of the elements shown.

DETAILED DESCRIPTION OF THE PRESENT INVENTION

[First Embodiment]

Figure 1:
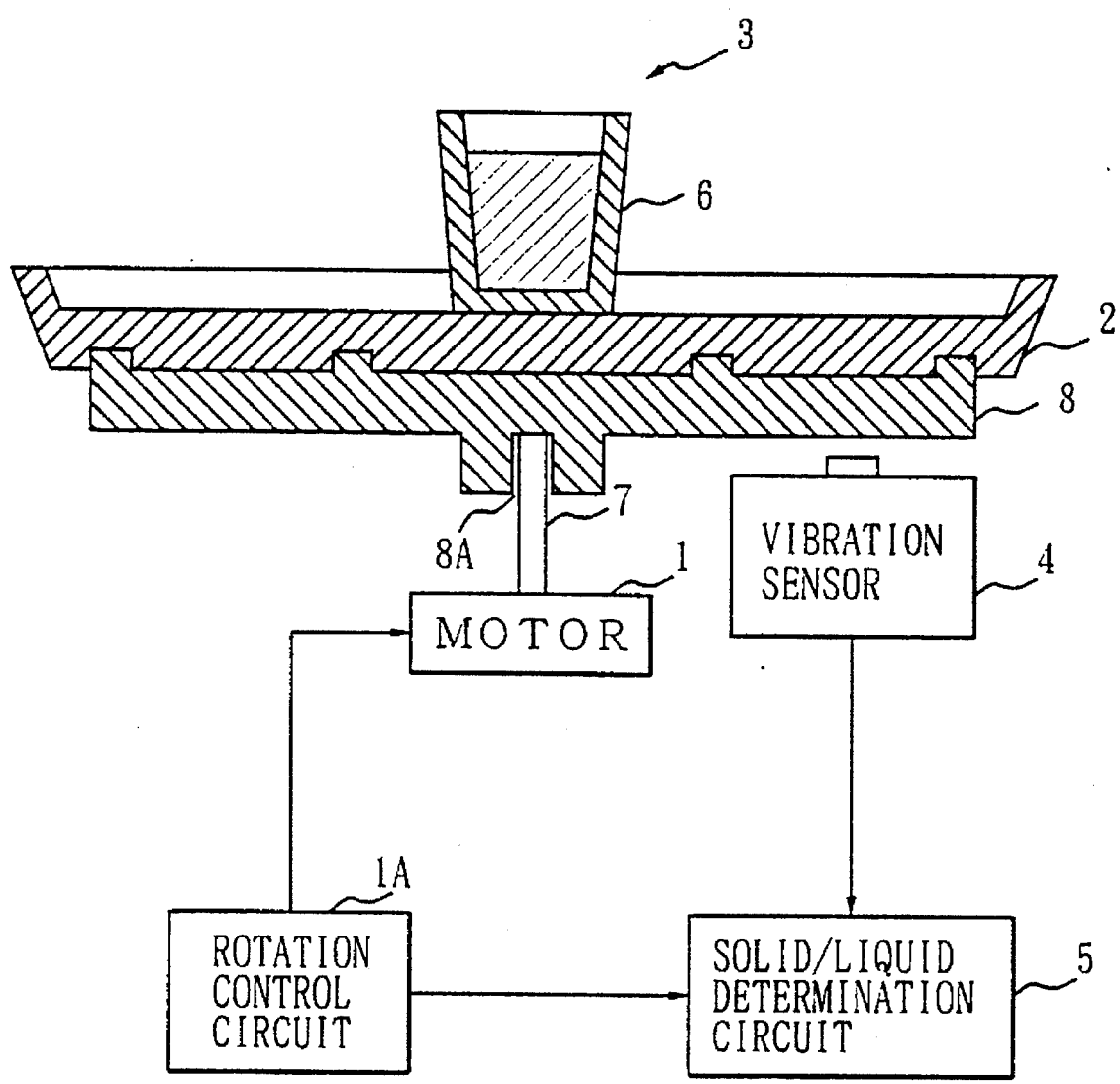
FIG. 1 is a cross-sectional side view of the solid/liquid determination apparatus of a first embodiment of the present invention.
Figure 2A:
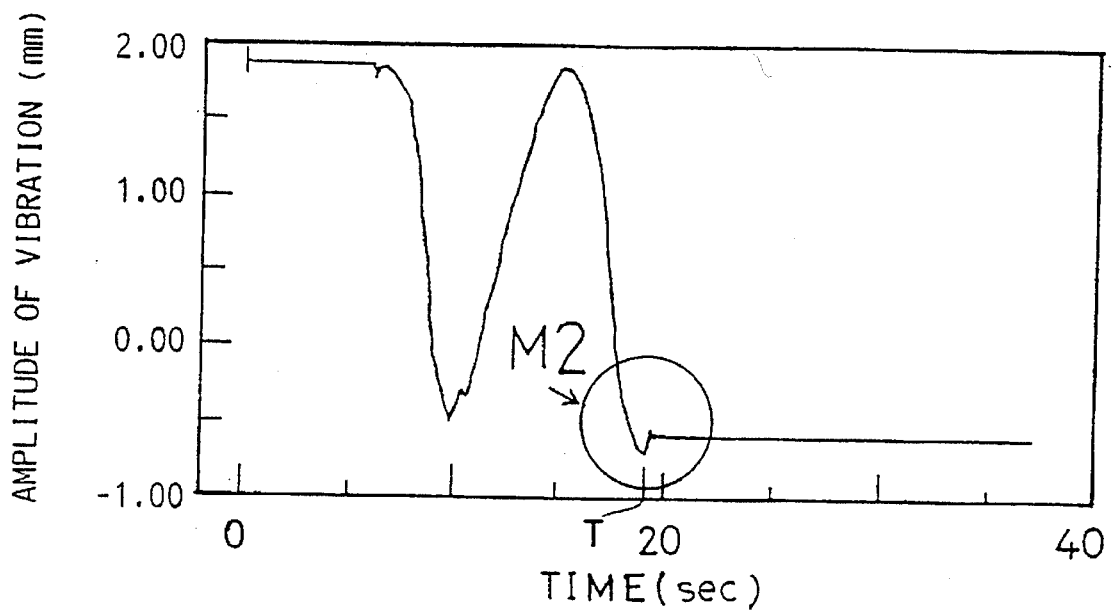
FIG. 2A is a diagram representing a vibration in liquid versus time in the solid/liquid determination apparatus of the first embodiment.
Figure 2B:
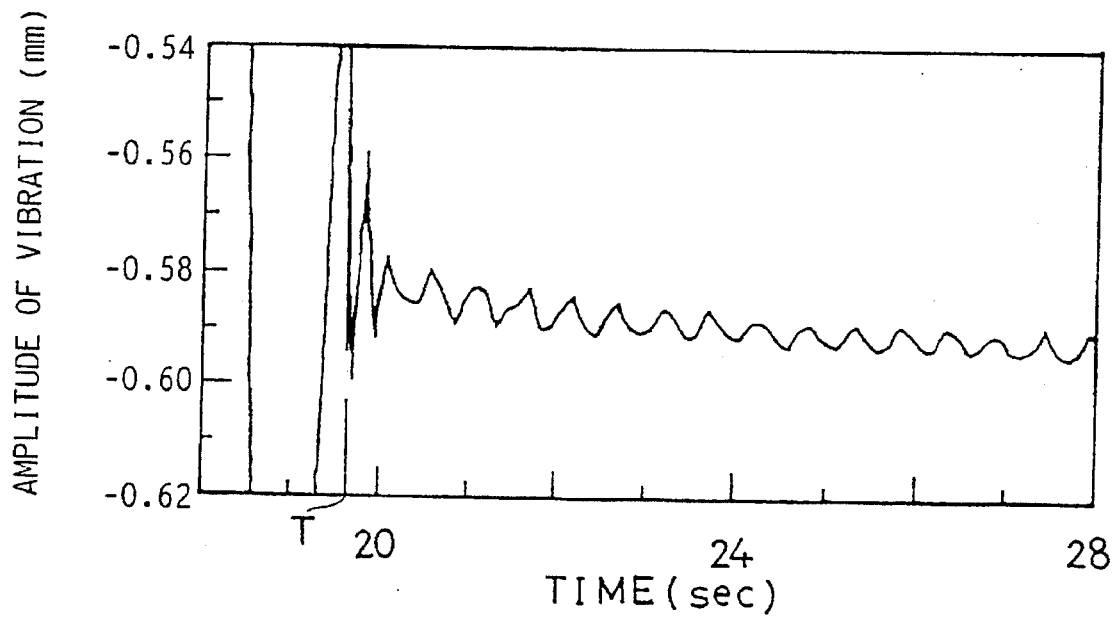
FIG. 2B is a diagram enlarging a circular region M2 of FIG. 2A.

FIG. 1 is a cross-sectional side view of the solid/liquid determination apparatus of a first embodiment in accordance with the present invention. A holding member 8 is coupled to a rotation shaft 7 of a motor 1, and a turntable 2 is connected to the holding member 8. The rotation shaft 7 is inserted in a hole 8A of the holding member 8. The inner diameter of the hole 8A is made larger than the diameter of the rotation shaft T, so that the rotation shaft 7 is loosely inserted in the hole 8A so as to be able to remove easily. An object 3 to be determined is put on the turntable 2. A vibration sensor 4 is disposed under the holding member 8, and vibration of the turntable 2 is detected thereby. Output of the vibration sensor 4 is inputted to a solid/liquid determination circuit 5. The vibration sensor 4 is a non-contact displacement gauge such as a laser distance gauge. Such a vibration sensor 4 is presently marketed by several companies. The rotation of the motor i is controlled by a rotation control circuit 1A. The object 3 is composed of a ceramic container 6 of 300 g (gram) in weight and 1700 g of water filled in the container 8. Consequently, the total weight of the object 3 is 2000 g. Using the above-mentioned configuration, the following experiment is performed:

After the turntable 2 is kept to a stationary state during seven seconds, the turntable 2 is rotated by the motor 1 under the control of the rotation control circuit 1A. FIG. 2A is a time diagram representing the vibration of the turntable 2. Referring to FIG. 2A, the turntable 2 vibrates vertically by rotation of the motor 1, and a signal of a roughly sinusoidal waveform is output from the vibration sensor 4. This vertical vibration is caused by swing of the turntable 2 because of a gap between the rotation shaft V and the hole 8A. The rotation of the motor 1 is stopped at a time T after the rotation of about ten seconds. Even after the stop of the motor 1, the turntable 2 vertically vibrates. In order to observe the vibration in detail, a region indicated by a circle M2 in FIG. 2A is enlarged as shown in FIG. 2B. Referring to FIG. 2B, after the stop of the rotation of the turntable 2, it vibrates with a minute amplitude of vibration during ten and several seconds at an approximately constant frequency.

Figure 3A:
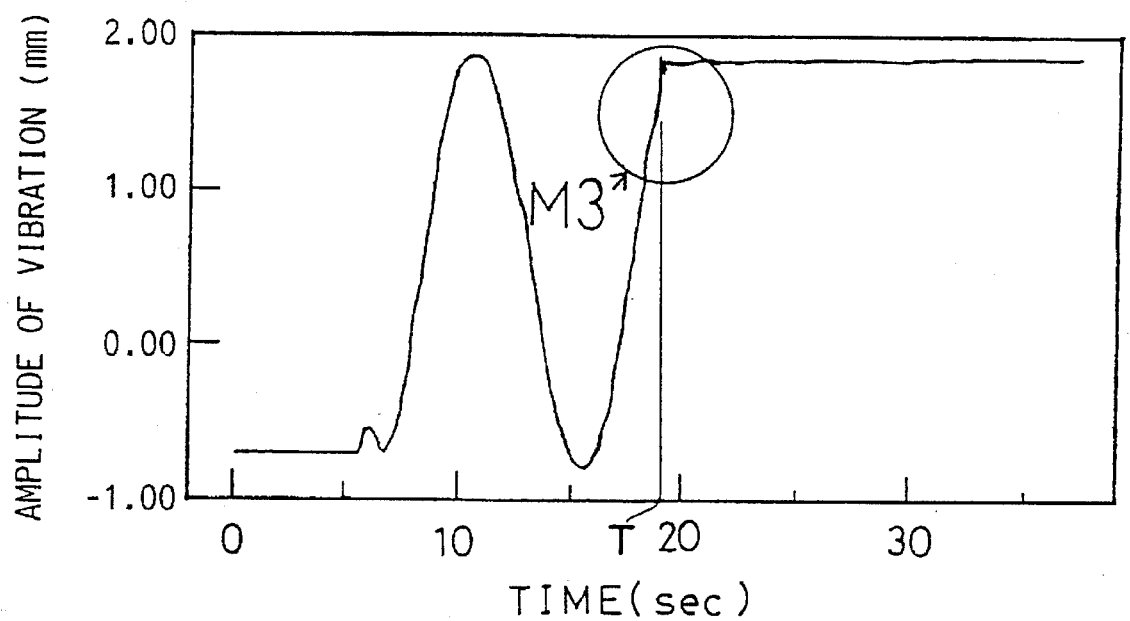
FIG. 3A is a diagram representing a vibration in solid versus time in the solid/liquid determination apparatus of the first embodiment.
Figure 3B:
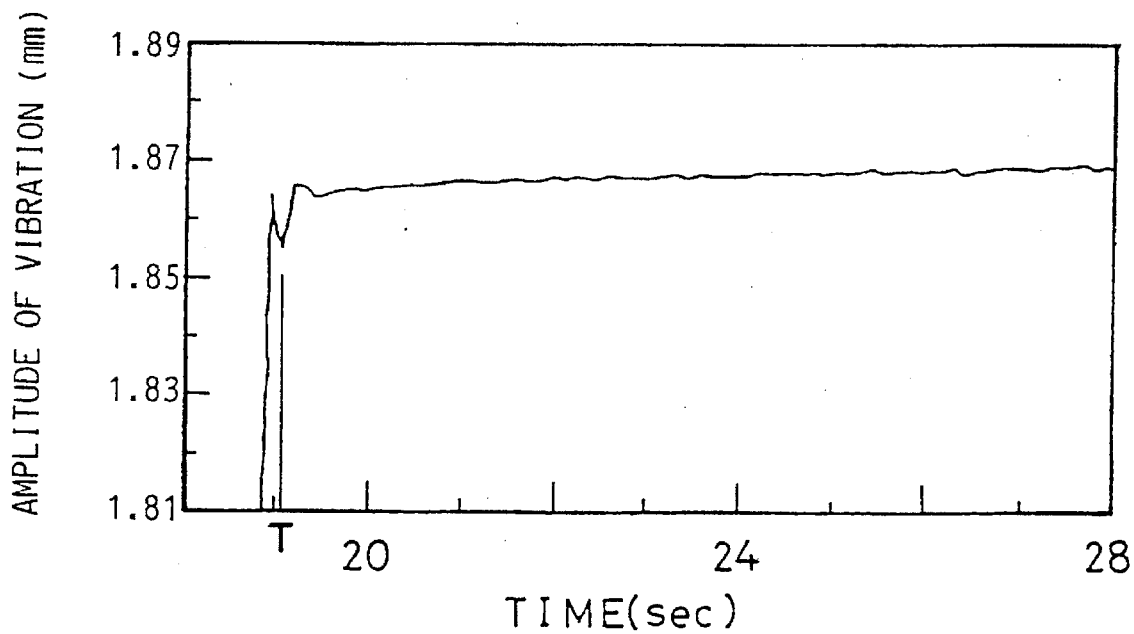
FIG. 3B is a diagram enlarging a circular region M3 of FIG. 3A.

Subsequently, the container 6 is replaced with an iron block of 2000 g in weight (not shown), and the same experiment as the container 6 with the water is performed in substantially the same process. FIG. 3A and FIG. 3B are diagrams representing vibrations of the turntable 2 in this case. A region indicated by a circle M3 in FIG. 3A is enlarged as shown in FIG. 3B. As shown by the diagram in FIG. 3B, the turntable 2 hardly vibrates after the stop of the rotation of the turntable 2 at the time T. And, the following conclusions are drawn from the above-mentioned experiments:

(1) In the case that the object 3 comprises liquid such as water, when the turntable 2 is stopped after the rotation of a predetermined time period, the turntable 2 vibrates at a constant frequency, and the vibration continues for more than ten and several seconds. The vibration is caused by occurrence of wave in the liquid.

(2) On the contrary, in the case that the object 3 is a solid, when the turntable 2 is stopped after the rotation of the predetermined time period, the turntable 2 comes to a halt within about one second, and maintains a stationary state thereafter.

In the first embodiment, the output of the vibration sensor 4 is applied to the solid/liquid determination circuit 5, and the object 3 is determined whether it is liquid or solid on the basis of the presence or absence of the vibration after the turntable is stopped.

In the solid/liquid determination circuit 5, a reference level of the amplitude of vibration is predetermined. The output of the vibration sensor 4 is compared with the reference level after the rotation of the turntable 2 is stopped. The operation of the solid/liquid determination circuit 5 is described in detail with reference to FIG. 16.

Figure 16:
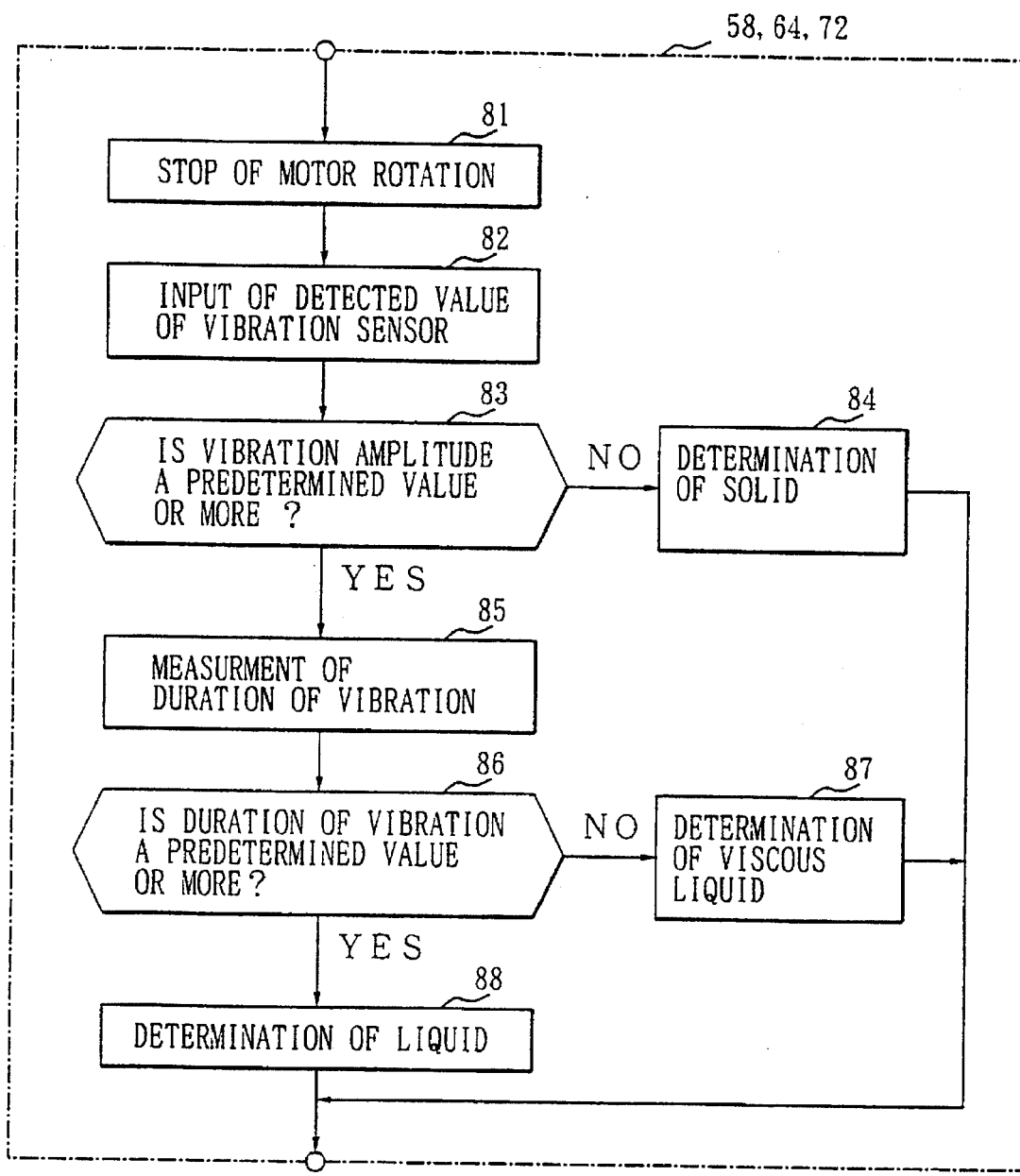
FIG. 16 is a flow chart of the operation of the solid/liquid determination apparatus of the first embodiment of the present invention.

Referring to FIG. 16, the rotation of motor 17 is temporarily suspended, at step 81. The output of the vibration sensor 18 is inputted to the solid/liquid determination circuit 19, at step 82, and the amplitude of vibration is compared with a predetermined value, at step 83. When the amplitude of vibration is smaller than the predetermined value, the state of the food is determined to be solid, at step 84. When the amplitude of vibration is the predetermined value or more, a duration of the vibration is measured at step 85. When the duration of the vibration is smaller than a predetermined time period, for example 5 seconds, in the comparison step 88, the state of food is determined to be viscous liquid, at step 87. When the duration is the predetermined time period or more, the state of food is determined to be liquid at step 88.

[Second Embodiment]

Figure 4:
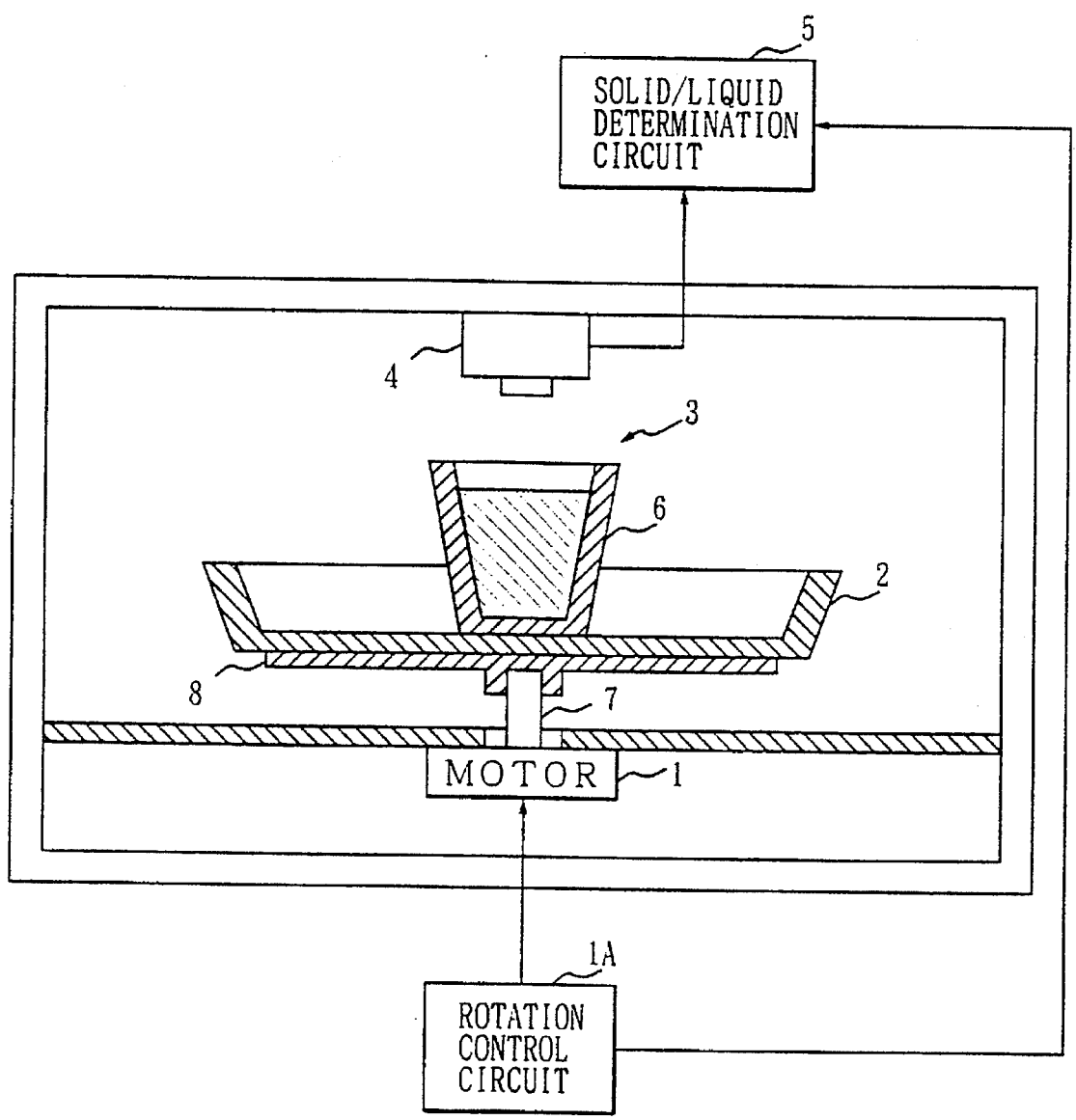
FIG. 4 is a cross-sectional side view of the solid/liquid determination apparatus of a second embodiment of the present invention.

FIG. 4 is a cross-sectional side view of the second embodiment of the solid/liquid determination apparatus. In the second embodiment, the vibration sensor 4 such as a laser displacement gauge or an ultrasonic displacement gauge is disposed over the object 3 in opposed relationship to the object 3, and detects vibration of the surface of the object 3. The rotation shaft 7 of the motor 1 is fixed on the holding member 8, and the turntable 2 mounted on the holding member 8 is rotated by the motor 1. The motor 1 is controlled by the rotation control circuit 1A in a manner similar to the first embodiment.

The vibration of the object 3 is directly detected by the vibration sensor 4 in the second embodiment. The output of the vibration sensor 4 is applied to the solid/liquid determination circuit 5. In the case of liquid in the object 3, after the turntable 2 is stopped, the surface of the liquid waves during ten and several seconds. On the contrary, in the case of solid, the surface of the object 3 does not vibrate, and the vibration of the turntable 2 comes to a halt within about one second. Consequently, the state of the object 3 is determined by the solid/liquid determination circuit 5 whether it is solid or liquid.

[Third Embodiment]

Figure 5:
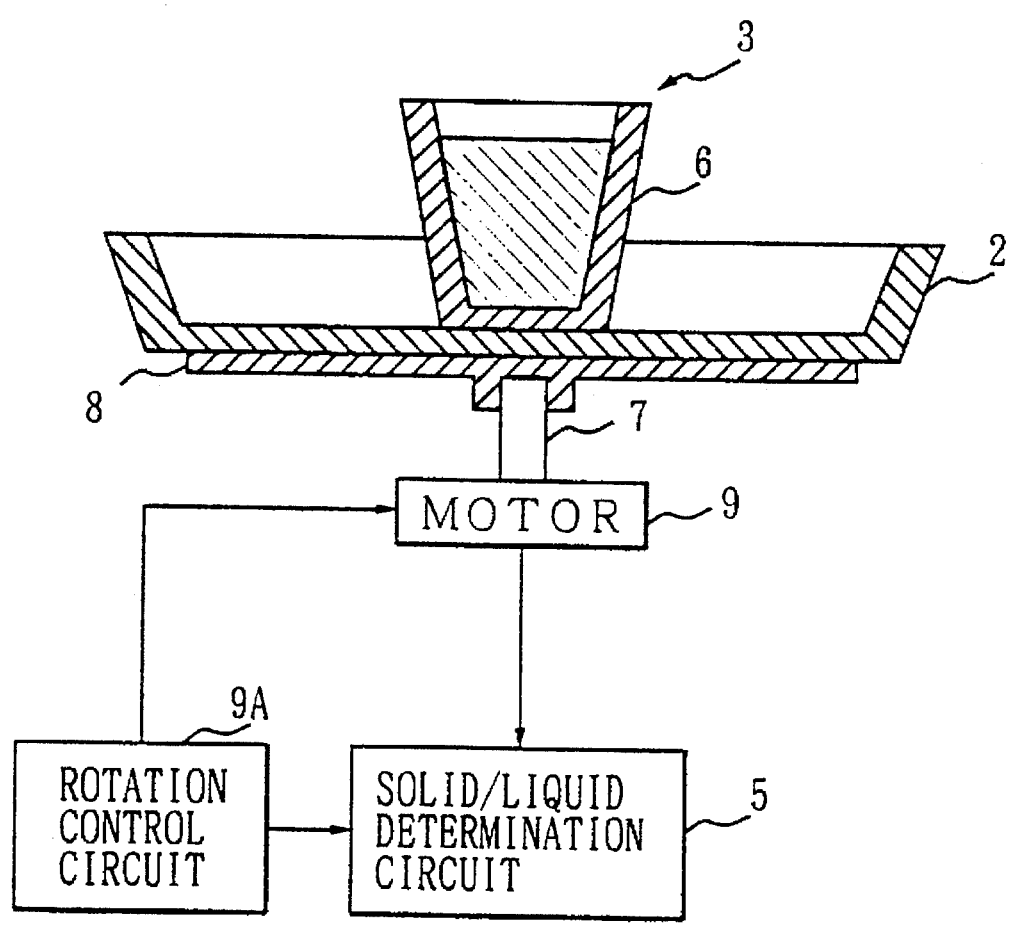
FIG. 5 is a cross-sectional side view of the solid/liquid determination apparatus of a third embodiment of the present invention.

FIG. 5 is a cross-sectional side view of the third embodiment of the solid/liquid determination apparatus. In the third embodiment, an induction motor 9 is used as replacement for the motor 1 in the previous embodiment. The vibration sensor 4 is not used. When the rotation shaft 7 of the induction motor 9 is rotated in the state that an electric input is not supplied to the induction motor 9, a current is induced in response to the rotation of the rotation shaft 7. The induced current is applied to the solid/liquid determination circuit 5 through a resistor for converting the induced current to a voltage.

Figure 6A:
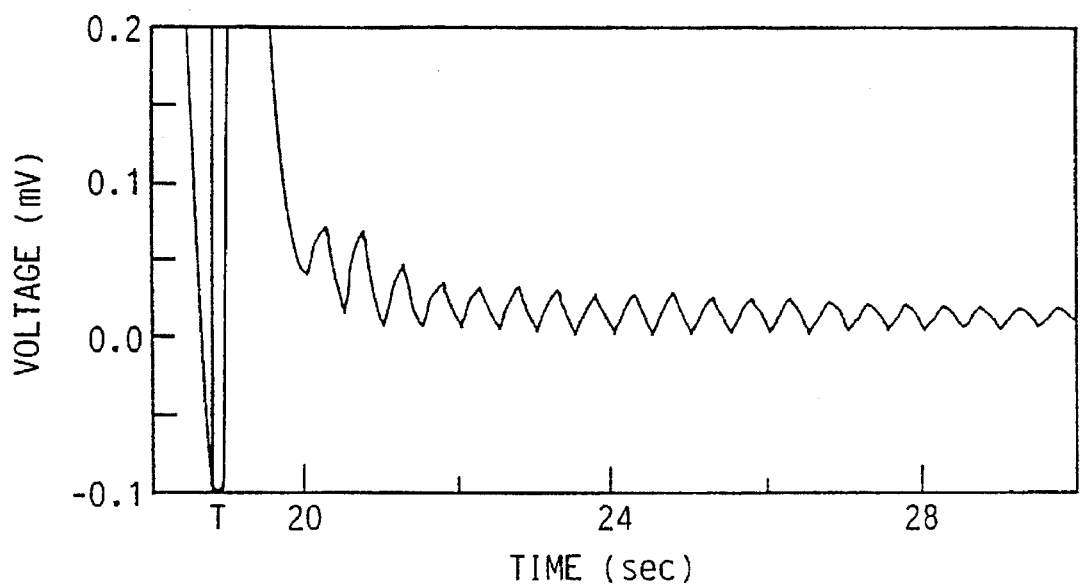
FIG. 6A is a diagram representing a detected current versus time in liquid in the solid/liquid determination apparatus of the third embodiment.
Figure 6B:
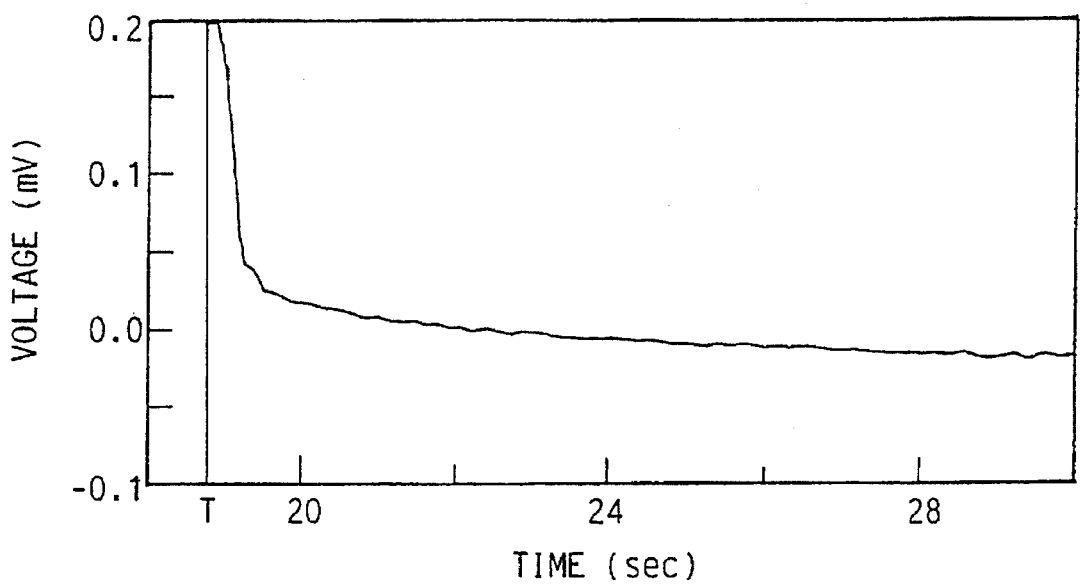
FIG. 6B is a diagram representing a detected current versus time in solid in the solid/liquid determination apparatus of the third embodiment.

In a manner similar to the first embodiment, the turntable 2 mounted with the object 3 is rotated by the motor 9, and after rotation for a predetermined time period, the motor 9 is stopped by the control of the rotation control circuit 9A at the time T. Consequently, in the case of the object 3 containing liquid, some forces are applied to the rotation shaft 7 to rotate it in normal rotation direction and to that in reverse rotation direction by the vibration of the liquid through the turntable 2 for more than ten and several seconds. Consequently, a vibration current is generated as shown in FIG. 6A. On the contrary, in the case of the object 3 of solid, the vibration current is hardly generated as shown in FIG. 6B. As mentioned above, the state of the object is determined. According to the third embodiment, the structure of the solid/liquid determination apparatus is simplified because the vibration sensor 4 may be dispensed with.

[Fourth Embodiment]

Figure 7A:
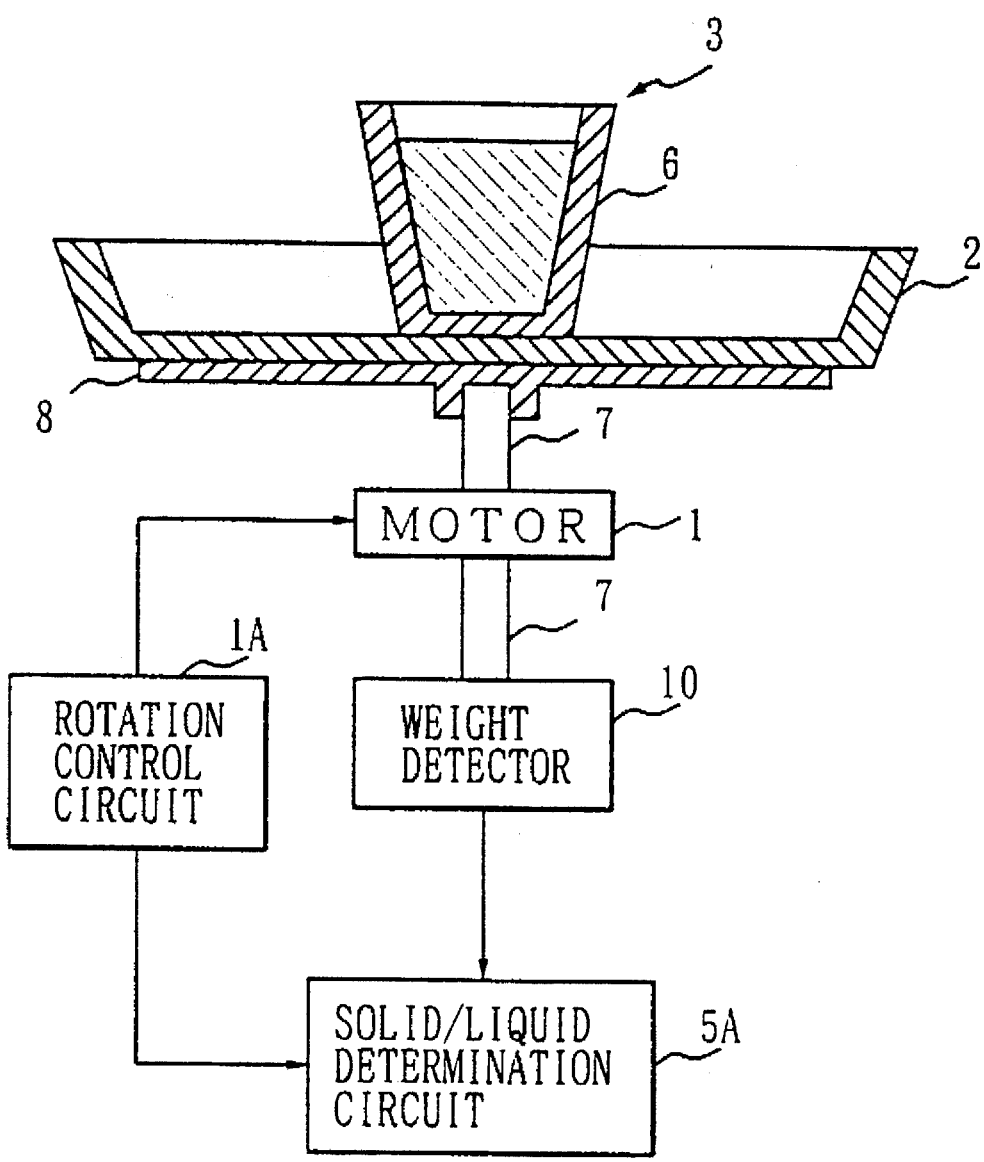
FIG. 7A is a cross-sectional side view of the solid/liquid determination apparatus of a fourth embodiment of the present invention.

FIG. 7A is a cross-sectional side view of the fourth embodiment of the solid/liquid determination apparatus of the present invention. In the embodiment, a weight sensor 10 for detecting a weight is disposed on a rotation shaft 7A passing through the motor 1. The weight sensor 10 detects the weights of the object 3, the turntable 2 and the motor 1 which are applied to the rotation shaft 7A, and the detected output is applied to the solid/liquid determination circuit 5A.

Figure 7B:
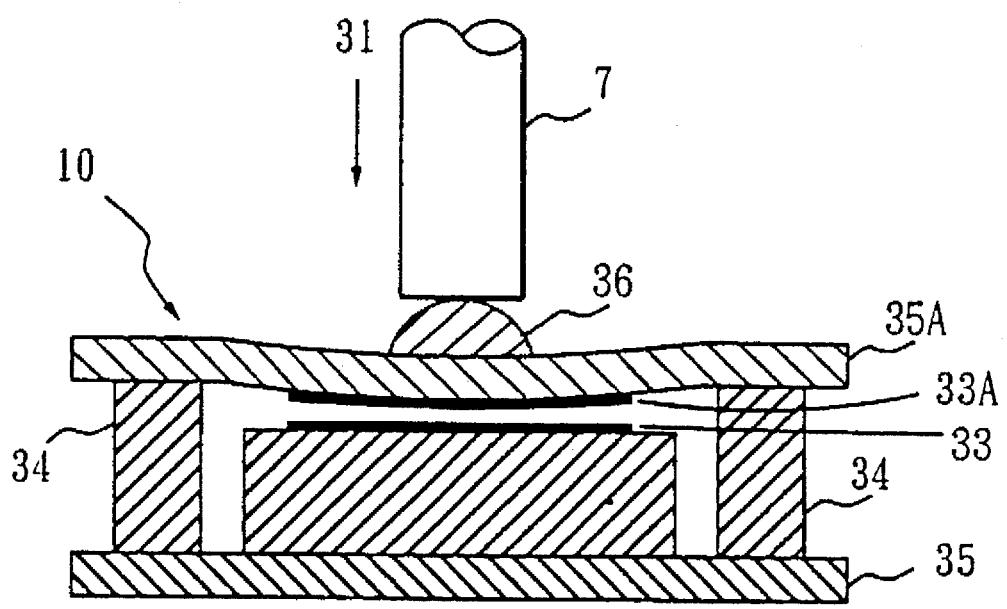
FIG. 7B is a detailed cross-section of a weight sensor which is used in the solid/liquid determination apparatus of the fourth embodiment.

FIG. 7B is a cross-sectional side view illustrating a detailed structure of the weight sensor 10. A circular electrode 33 of about 15 mm in diameter is formed on an upper surface of an alumina substrate 35 of about 30 mm in diameter, for example. An opposite electrode 33A to the electrode 33 is formed on the lower surface of another alumina substrate 35A. Both the substrates 35 and 35A are assembled by sealing glass 34 so that the interval between both the electrodes 33 and 33A is sealed and kept to about 45 microns. A lower end of the rotation shaft 7 is coupled to a load reception end 38 disposed at a center of the alumina substrate 35A. When a load is applied to the load reception end 38 in the direction shown by an arrow 31. As shown in FIG. 7B, the substrate 35A is deformed, and a distance between both the electrodes 33 and 33A is reduced. Consequently, a capacitance between both the electrodes 33 and 33A increases. The solid/liquid determination circuit 5A is provided with a detection circuit comprising a CR oscillator for detecting a change of frequency corresponding to the variation of the capacitance. Consequently, the vibration of the turntable 2 may be detected on the basis of the change of frequency. The same experiment as the condition in the first embodiment is performed in the fourth embodiment. The frequency change versus time based on the output of the weight sensor 10 is illustrated in FIG. 8A and FIG. 8B.

Figure 8A:
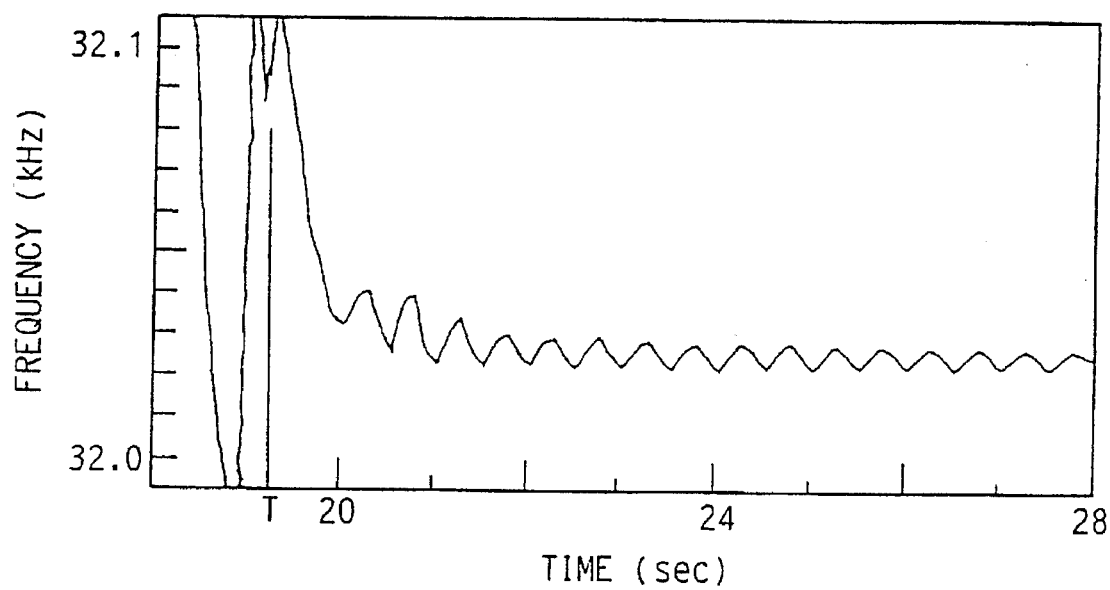
FIG. 8A is a diagram representing a vibration in liquid versus time in the solid/liquid determination apparatus of the fourth embodiment.
Figure 8B:
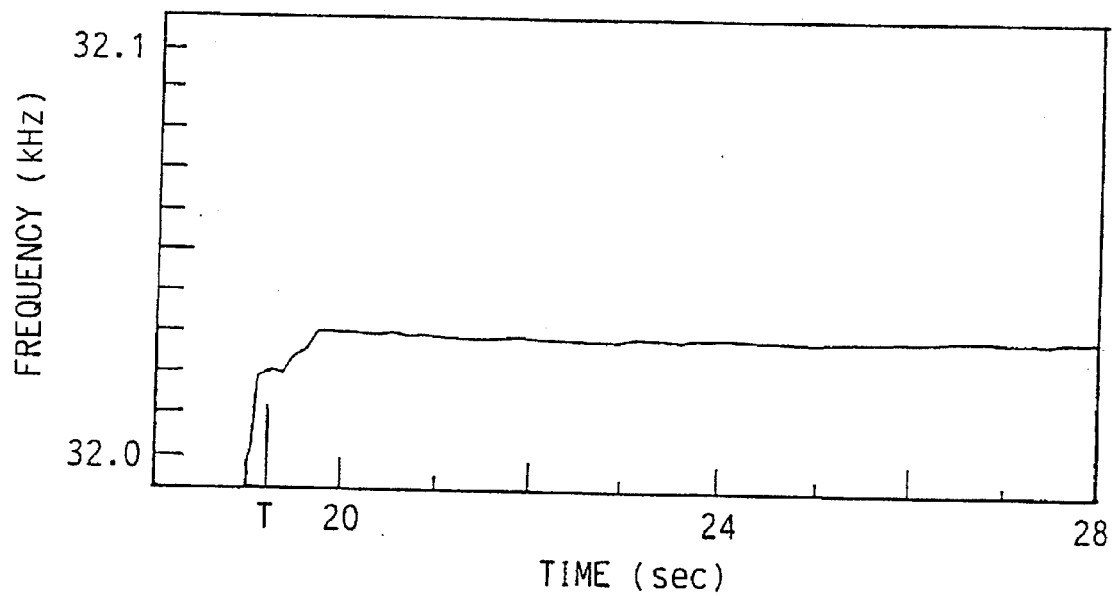
FIG. 8B is a diagram representing a vibration in solid versus time in the solid/liquid determination apparatus of the fourth embodiment.

FIG. 8A is a diagram representing the frequency change versus time in the case of liquid as the content of the object 3. After the turntable 2 is stopped at the time T, the frequency varies 5–10 Hz during more than 10 seconds. On the contrary, FIG. 8B is a diagram illustrating a variation of frequency versus time in the case of solid as the object 3. A variation of frequency settles down within about 1 second after the time T, and the frequency becomes a constant. Consequently, the state of solid or liquid can be determined on the basis of the variation of frequency.

[Fifth Embodiment]

Figure 9A:
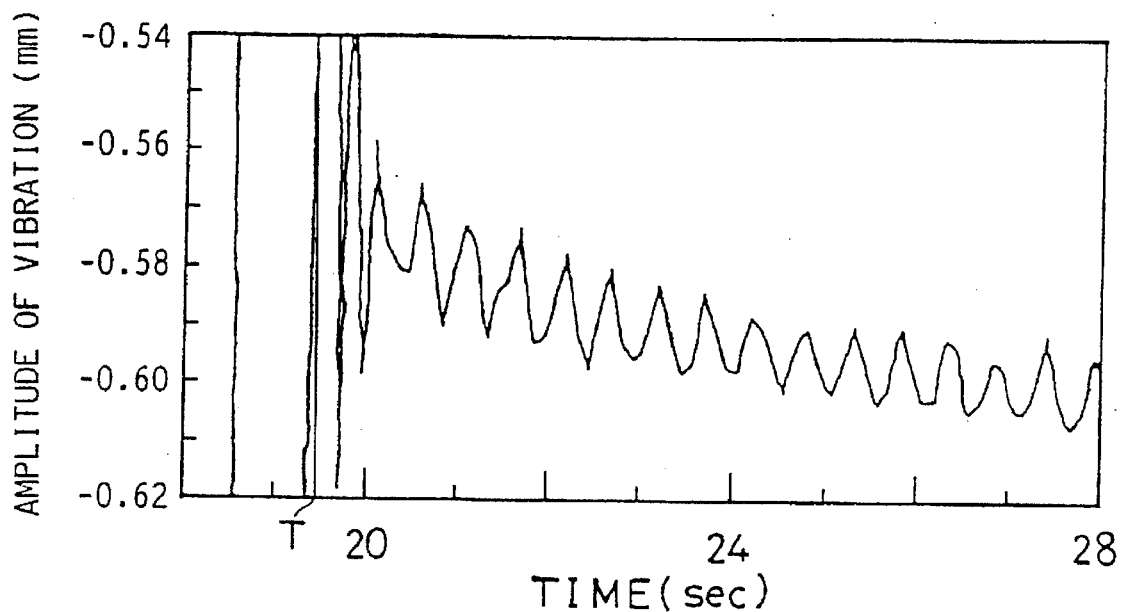
FIG. 9A is a diagram representing a vibration in liquid versus time in the solid/liquid determination apparatus of a fifth embodiment.
Figure 9B:
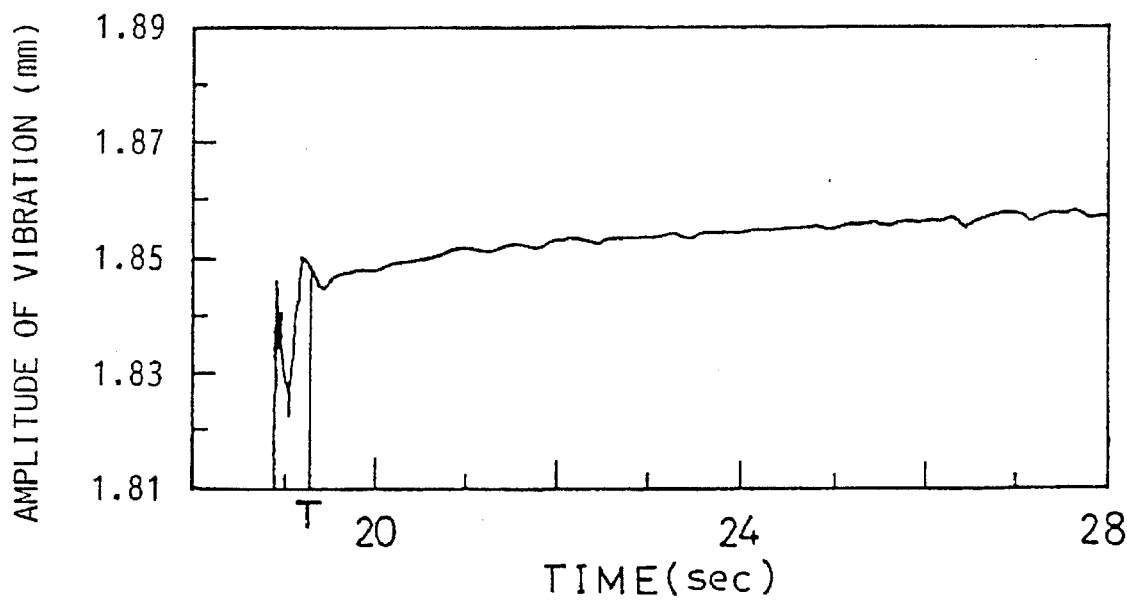
FIG. 9B is a diagram representing a-vibration in solid versus time in the solid/liquid determination apparatus of the fifth embodiment.

In the fifth embodiment, in the same configuration as the first embodiment as shown in FIG. 1, first, the turntable 2 having the same object 3 as the condition of the first embodiment is rotated for about 10 seconds, and subsequently, the direction of rotation of the turntable 2 is reversed. The turntable 2 is stopped after the reverse rotation for several seconds. Consequently, in the case that the content of the object 3 is liquid, as shown in FIG. 9A, the amplitude of vibration after the time T at which the reverse rotation is stopped becomes as twice large as the amplitude of vibration shown in FIG. 2B of the first embodiment. This is caused by generation of a large vibration by inertia of the liquid in the container 6. On the contrary, in the case of the solid, as shown in FIG. 9B, the amplitude of vibration after the time T is substantially equal to the amplitude in FIG. 3B of the first embodiment. Consequently, the amplitude of vibration in the liquid is greatly different from the amplitude of vibration in the solid, and the determination of solid or liquid can be easily made in comparison with the first embodiment.

[Another Experiment in the Fifth Embodiment]

In the fifth embodiment, the following three samples are prepared for the object 3:

Sample (1): 1700 g of water is filled into the container 6 of 300 g in weight

Sample (2): 1700 g of iron chips put in the container 3 of 300 g in weight

Sample (3): 700 g of water and 1000 g of iron chips put in the container 6 of 300 g in weight.

Figure 10:
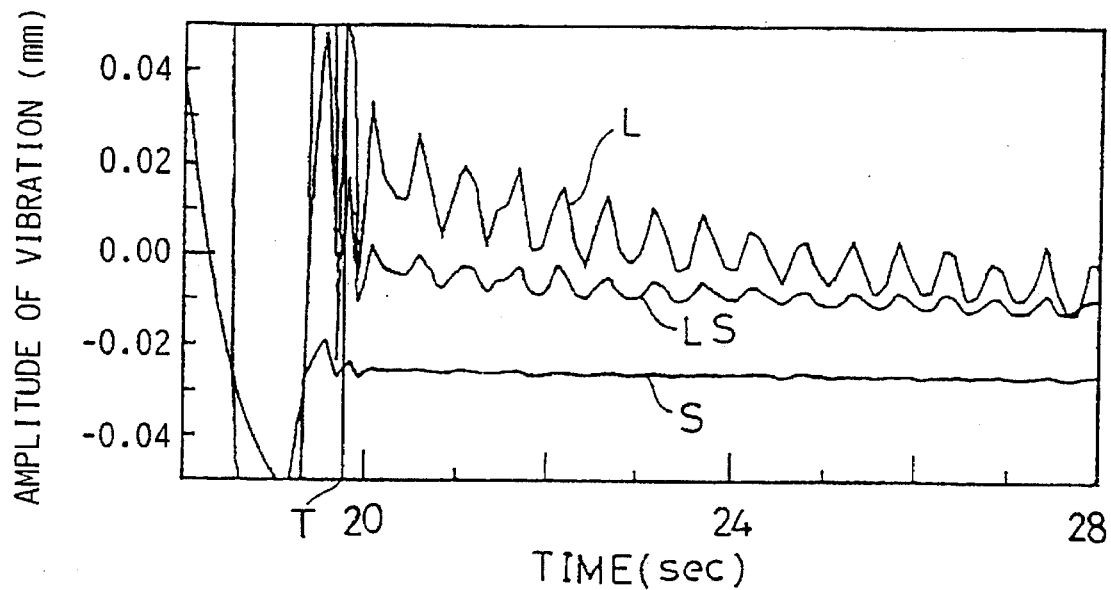
FIG. 10 is a diagram representing a vibration of a mixture of solid and liquid versus time in the solid/liquid determination apparatus of the fifth embodiment.

After the turntable 2 is rotated for about 10 seconds, the rotation direction is reversed. After the turntable is rotated in the reverse rotation direction for several seconds, the rotation of the turntable 2 is stopped. Then the vibration of the turntable 2 is detected by the vibration sensor 4 as shown in FIG. 1. FIG. 10 is a diagram representing the result of the experiment.

Referring to FIG. 10, a curve L represents a vibration waveform in the case of the Sample 1, and after the turntable 2 is stopped at the time T, the vibration of about 0.02 mm in the amplitude of the vibration continues for more than 10 seconds.

A curve S represents a vibration waveform in the case of the Sample 2, and after the turntable 2 is stopped at the time T, the amplitude of vibration is very small.

A curve LS represents a vibration waveform in the case of the Sample 3, and after the turntable 2 is stopped, the vibration of about 0.005 mm in the amplitude of vibration continues during more than 10 seconds. According to the above-mentioned results, the amplitude of vibration in the Sample 3 is about one fourth the amplitude in the Sample 1, and thus the Sample 1 can be distinguished from the Sample 3 on the basis of difference of the respective amplitudes. As a result, the state of the object 3, solid, liquid or mixture of the solid and liquid, can be individually determined.

Figure 11:
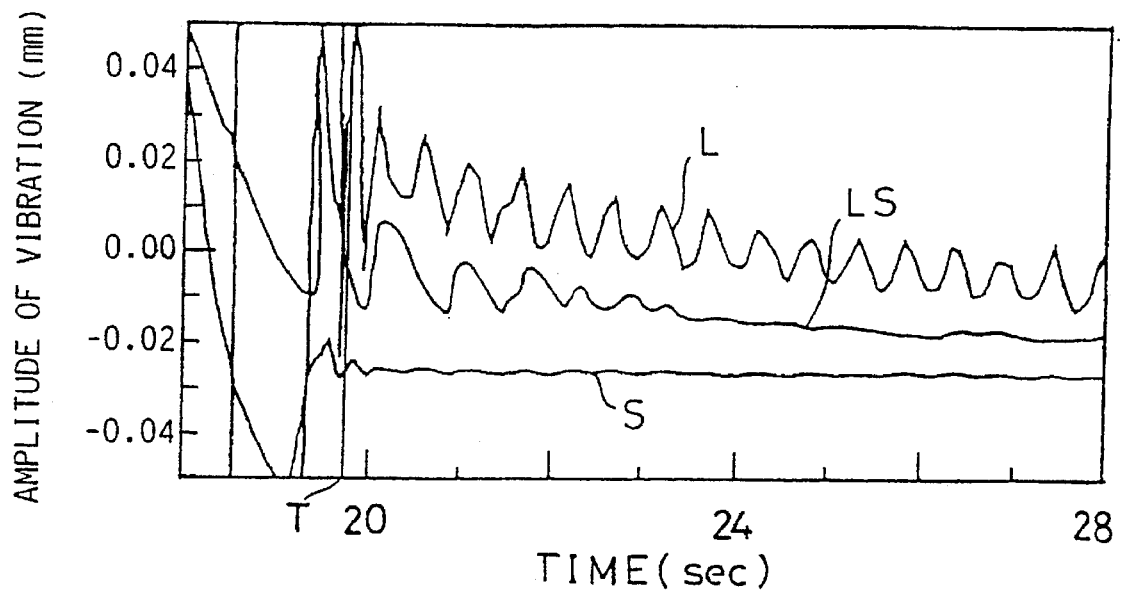
FIG. 11 is a diagram representing a vibration in viscous liquid versus times in the solid/liquid determination apparatus of the fifth embodiment.

Moreover, a Sample 4 is prepared. The Sample 4 comprises 1700 g of viscous liquid such as machine oil filled in the container 6 of 300 g in weight, and an experiment is performed with respect to the Sample 4 in a manner similar to the samples 1, 2 and 3. A result of experiment is shown in FIG. 11. A curve VL represents a vibration waveform in the case of the Sample 4. The curves L and S are the same as those in FIG. 10 and are illustrated for comparison purposes. In the case of the Sample 4 comprising the viscous liquid, an amplitude of vibration immediately after the turntable 2 is stopped at the time T is approximately equal to that of the curve L of the Sample 1. However, the amplitude of vibration rapidly decreases and approaches the amplitude of vibration of the curve S after several seconds.

According to the result of the above-mentioned experiment, since the duration of the vibration after the time T in the case of the viscous liquid is shorter than that in the case of the water, the viscous liquid can be distinguished by the water by the difference of the duration of the vibration.

In the above-mentioned first through fifth embodiments, the rotation of the turntable 2 is stopped, and the vibration after the stop is detected. However, in other method, the rotation of the turntable 2 is not stopped, but is changed in the rotation speed. After the rotation speed of the turntable 2 has been changed, the vibration thereof can be detected.

[Sixth Embodiment]

Figure 12:
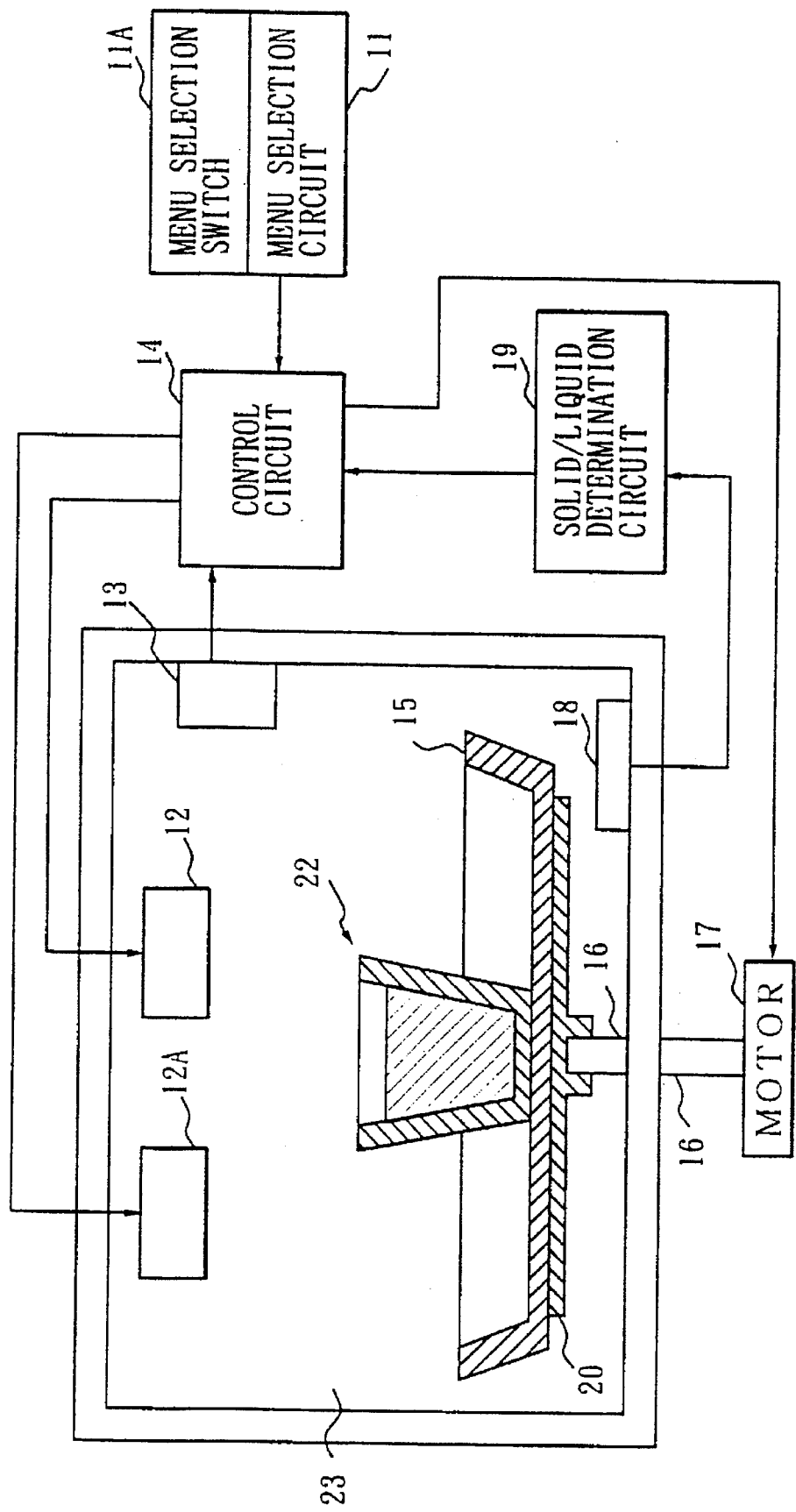
FIG. 12 is a block diagram of an automatic oven using the solid/liquid determination apparatus of a sixth embodiment of the present invention.

The sixth embodiment relates to an automatic oven using the solid/liquid determination apparatus of the above-mentioned first embodiment. FIG. 12 is a block diagram of the oven of the sixth embodiment. An electric heater 12 of a first heating means is disposed in a heating chamber 23, and heats the heating chamber 23. A microwave generator 12A of a second heating means is also disposed in the heating chamber 23. The electric heater 12 and the microwave generator 12A are alternatively activated by selection of an operator in accordance with kind of food. A turntable 15 is installed in the lower part of the heating chamber 23.

The turntable 15 is supported by a rotation shaft 16 introduced in the heating chamber 23 and is rotated by a motor 17 coupled to the rotation shaft 16. An object 22 to be heated is put on the turntable 15. A vibration sensor 18 is disposed under the turntable 15, and detects vibration of the turntable 15. A steam sensor 13 for detecting steam in the heating chamber 23 defined by a shield casing is disposed near the ceiling of the heating chamber 23. A heating state of a food may be detected by the steam sensor 13. Progress of cooking of the food may be indicated thereby. The steam sensor 13 is mounted preferably in an exhaust passageway (not shown in FIG. 12). The steam sensor 13 comprises a pyroelectric element and detects steam in the heating chamber 23 emanated from the object 22 to be healed. The detected outputs of the steam sensor 13 and the vibration sensor 18 are inputted to a control circuit 14. A menu selected by the operator with a menu selection switch 11A is set in a menu selection circuit 11, and the data of the menu is inputted to the control circuit 14. The control circuit 14 comprises a CPU and a memory (not shown), and controls the electric heater 12, microwave generator 12A and the motor 17 on the basis of the inputs of the steam sensor 1B, vibration sensor 18 and menu selection circuit 11. In the heating operation of the object 22, the motor 17 rotates the turntable 15. However, the motor 17 is temporarily stopped for 10–20 seconds every predetermined time interval. The vibration of the turntable 15 is detected by the vibration sensor 18 while the motor 17 is temporarily stopped, and the state of the object 22 is determined by means of the first embodiment.

Hereafter, operation of the sixth embodiment is described. Prior to start of the oven, a menu is selected by manipulating the menu selection switch 11A. The menus are selected from "MENU A" and "MENU B".

Menu A: for food which changes its state as a consequence of heating, e.g., butter (from solid to liquid), a food using an egg such as custard pudding and Chawan-mushi (custard-like egg and vegetable dish steamed in a cup) (from liquid to solid), Menu B: for food which does not change its state as a consequence of heating, e.g., soup, boiled rice, curry roux.

A heating constant K (hereafter is referred to simply constant K) is predetermined with respect to each food in the menus A and B. The constant K represents a relative heating time of a food, and the value of the constant K is large in the case of a food which is difficult to heat, for example soup, and is small in the case of boiled rice which is easy to heat. The constant K is derived by an experiment which will be described in detail hereafter. The constants K1–K6 with respect to several kinds of food are shown in Table 1. Values in parentheses in the Table 1 are an example of the constant K of the food. The name of a food listed in the Table 1 may be set in the menu selection circuit 11 as the menu A or the menu B.

TABLE 1

| Name of Food | Value of constant K |
| --- | --- |
| Boiled rice | K1 (0.1) |
| Soup | K2 (1.7) |
| Curry roux | K3 (0.8) |
| Butter | K4 (0.1) |
| Custard pudding | K5 (0.8) |
| Chawan-mushi | K6 (0.5) |

Figure 13:
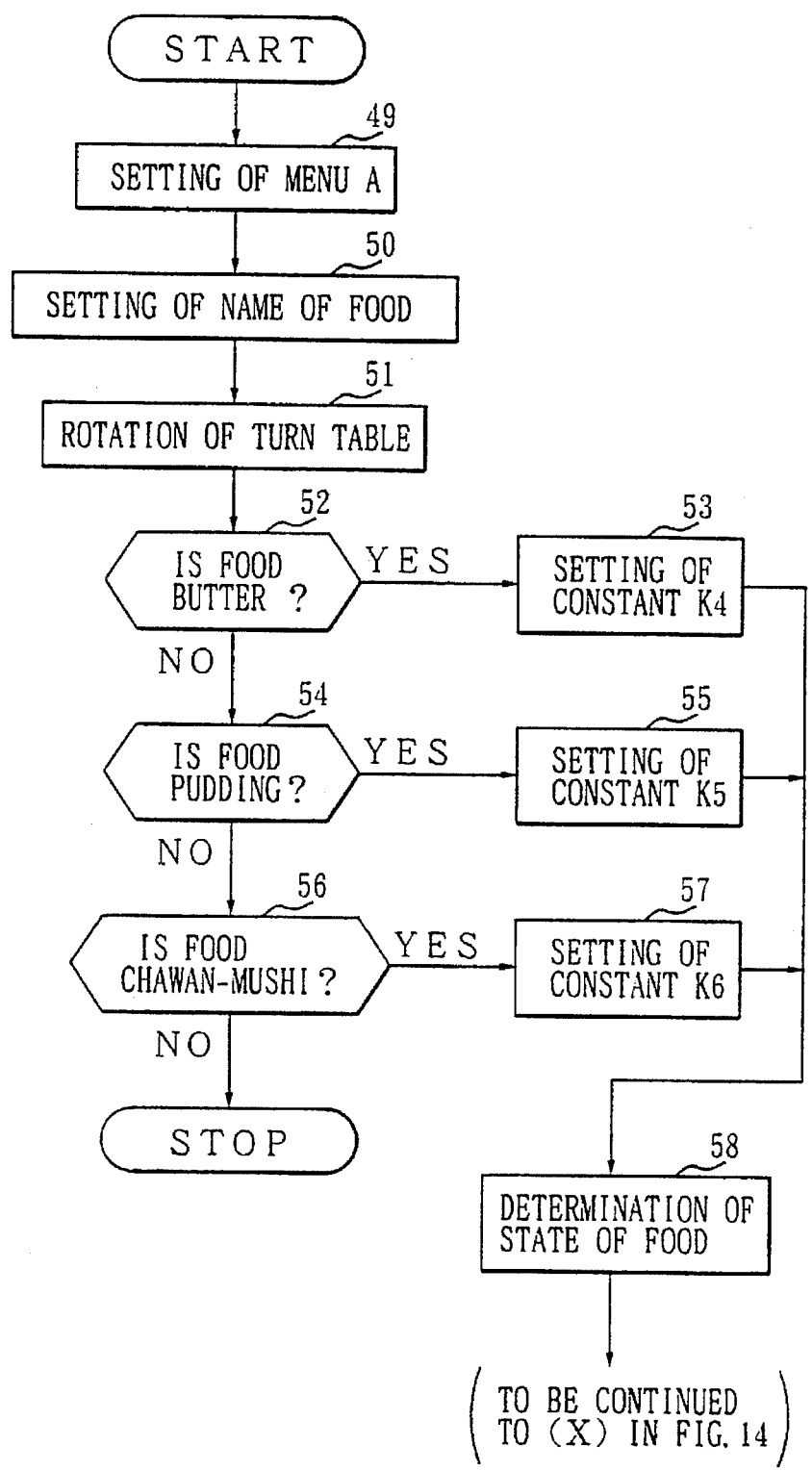
FIG. 13 is a flow chart of the operation of the automatic oven of the sixth embodiment.

FIG. 13 is a flow chart representing operation of the sixth embodiment of the automatic oven in the case of selection of a food in the menu A. After the menu A is set at step 49, the name of a food is set at step Three kinds of foods of butter, custard pudding and Chawan-mushi are set as cooking menus. Operation of the automatic oven is started at step 51, and the turntable 15 starts to rotate. The kind of food is determined at respective steps 52, 54 and 56, and the constant K predetermined as shown in the Table 1 with respect to each food is set at step 53, 55 or 57. Subsequently, the state of the food is determined at step 58. A detailed process of step 58 is illustrated in FIG. 16.

Figure 14:
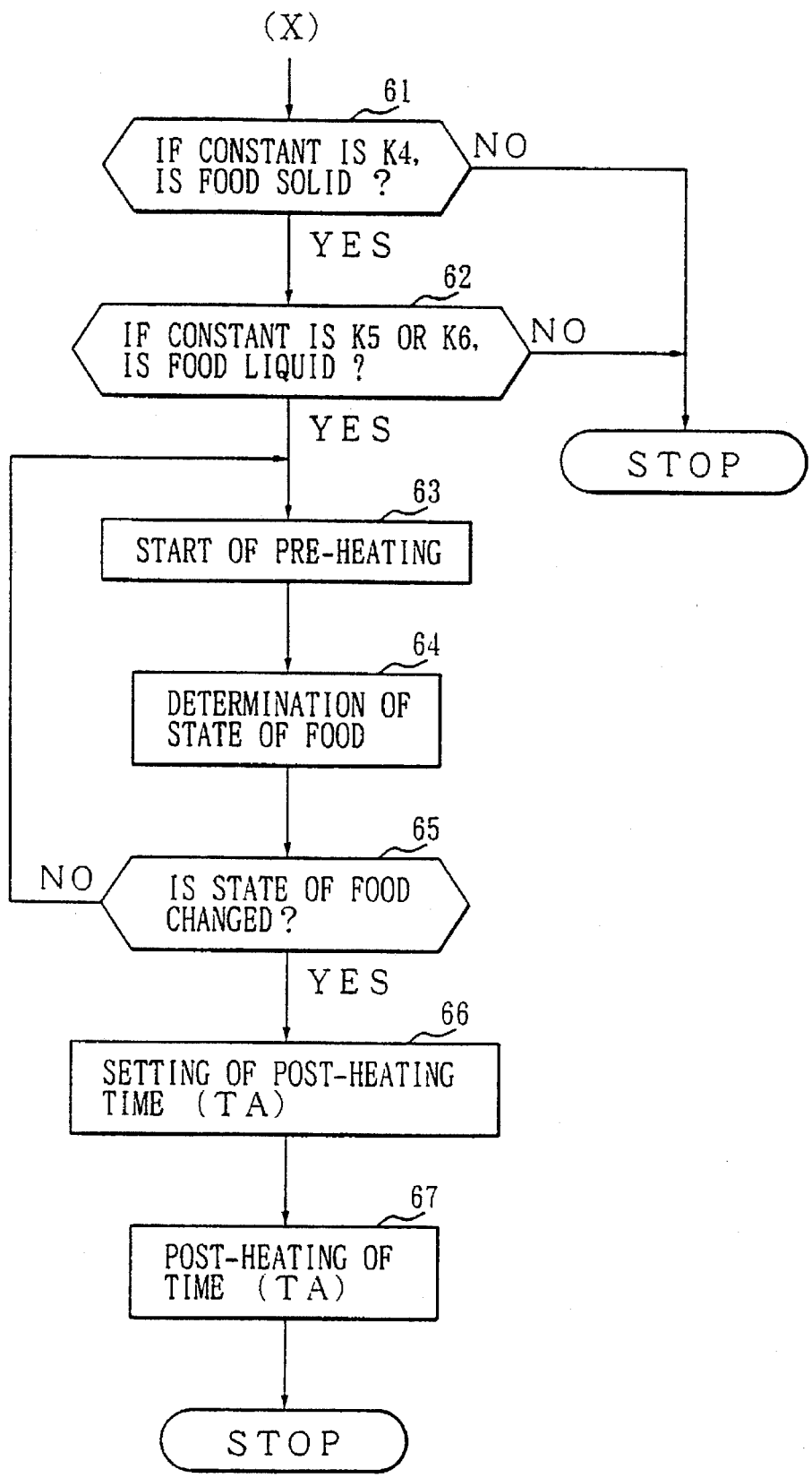
FIG. 14 is a flow chart to be combined with FIG. 3 of the operation of the automatic oven of the sixth embodiment.
Figure 18:
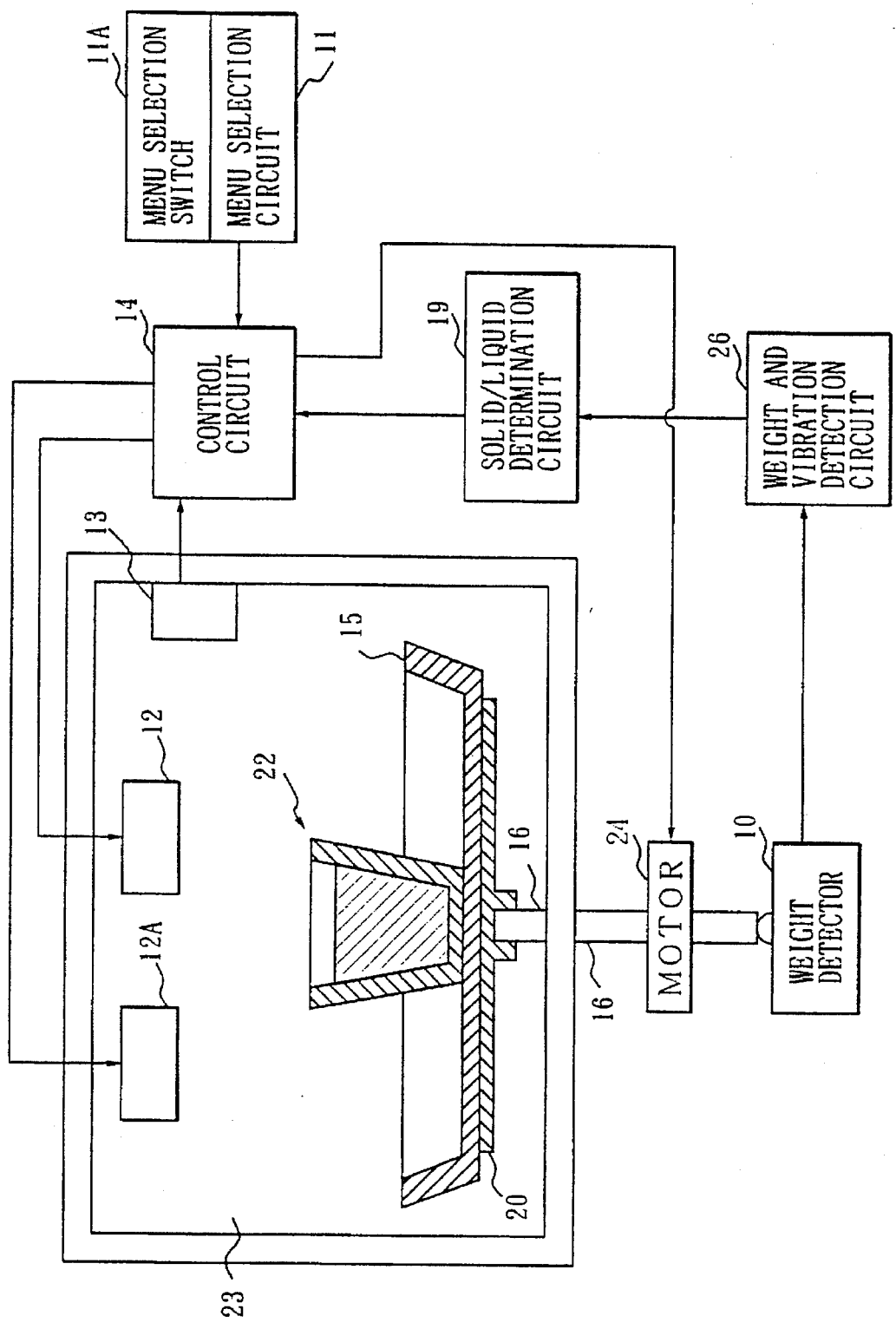
FIG. 18 is a block diagram of the automatic oven of a eighth embodiment using the solid/liquid determination apparatus of the fourth embodiment.
Figure 19:
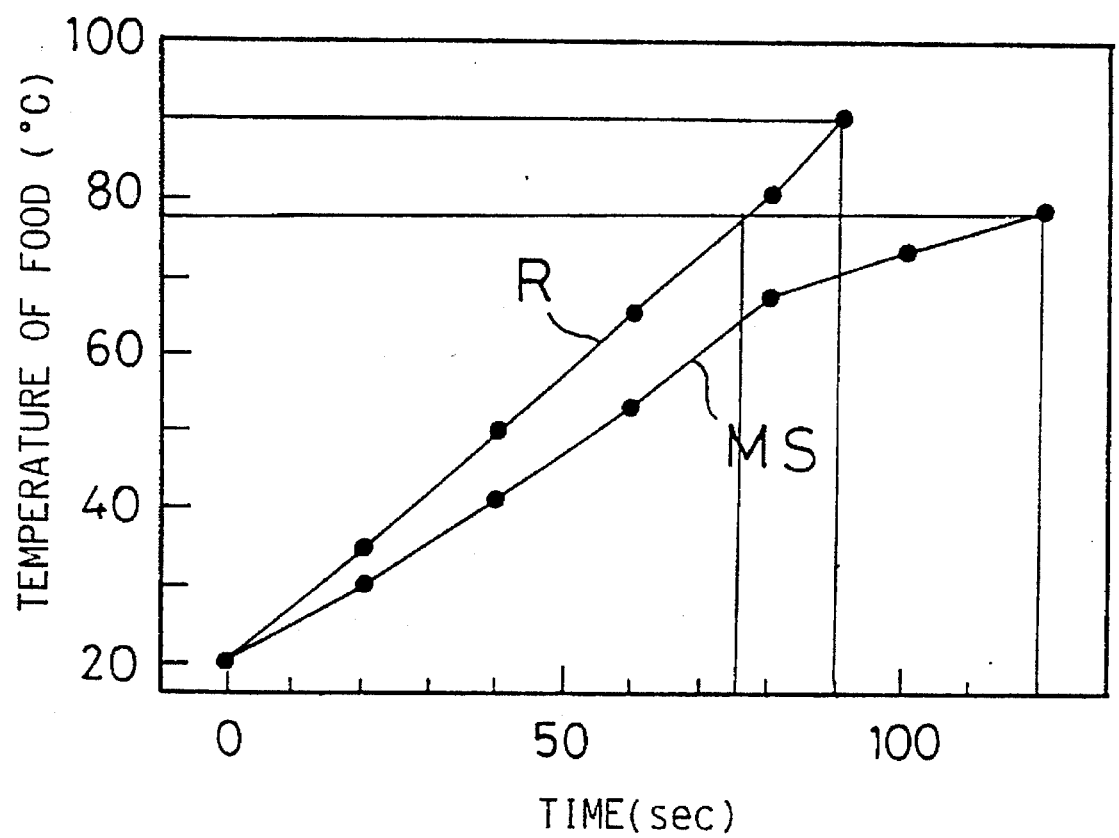
FIG. 19 is the diagram representing the temperatures of the boiled rice and the soup versus time in the prior art.
Figure 20:
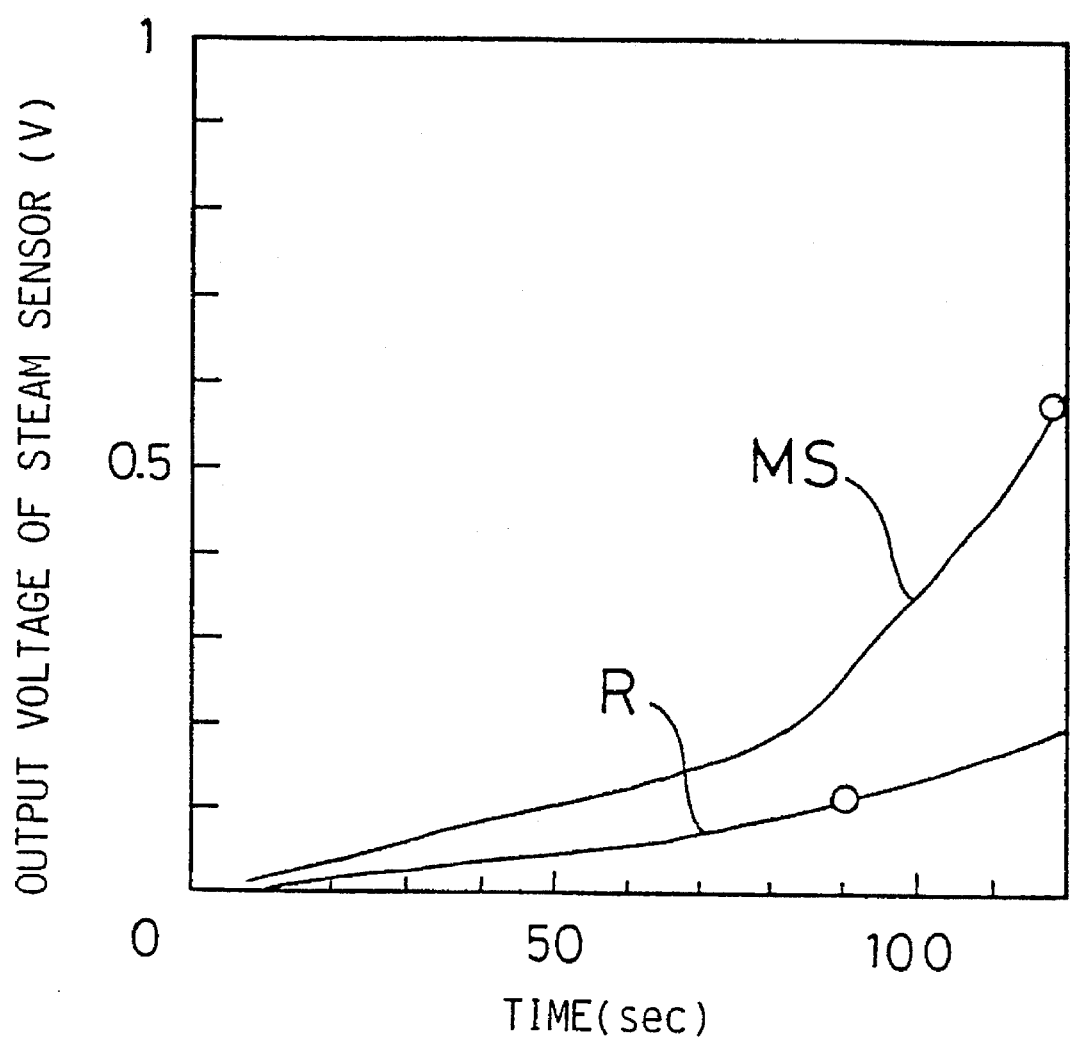
FIG. 20 is the diagram representing the outputs of the steam sensor versus time in the prior art.

Subsequently, in the decision step 61 in FIG. 14, when the constant K4 is set and the state determined at step 58 is not solid, it is determined that the butter corresponding to the constant K4 is melted or that, the setting operation in the menu selection circuit 11 is mistaken or the control circuit 14 is in malfunction. Consequently, the following operation of the automatic oven is suspended. After determination of solid at the step 61, in the case of selection of the constant K5 or KS, in the case of custard pudding or Chawan-mushi, it is determined whether the state is liquid at step 62. When the state is not liquid, it is determined that the heating of food is completed or the control circuit is in malfunction, and the following operation is suspended. When the state is determined to be liquid at step 62, a pre-heating operation is started at step 63. Choice of the electric heater 12 or the microwave generator 12A is left to the user. In general, for butter the heating by the microwave generator 12A is preferable, and for the custard pudding and Chawan-mushi the electric heater 12 is preferable. The state of food is determined every predetermined time interval also in the pre-heating operation, at step 64. The detailed process at step 64 is identical with that of the step 53 as shown in FIG. 18.

Change of the state of food is determined at step 65. When the state of food is maintained, the pre-heating operation is continued. When the change of the state of food is determined at step 65, a time period for a post-heating operation, which is an additional heating, is set at step 66. The post-heating operation performed at step 67 is for preventing presence of a half-cooked part in the custard pudding or the Chawan-mushi. A time period TA of the post-heating operation is the product of a time "t" by the constant K of the food set at step The time t is a time length from start of the pre-heating operation at step 63 to determination of the change of the state of food at step 65. For example, in the case of the custard pudding, since the constant K5 is 0.8, the time period TA of the post-heating operation is (t×0.8) seconds.

Figure 15:
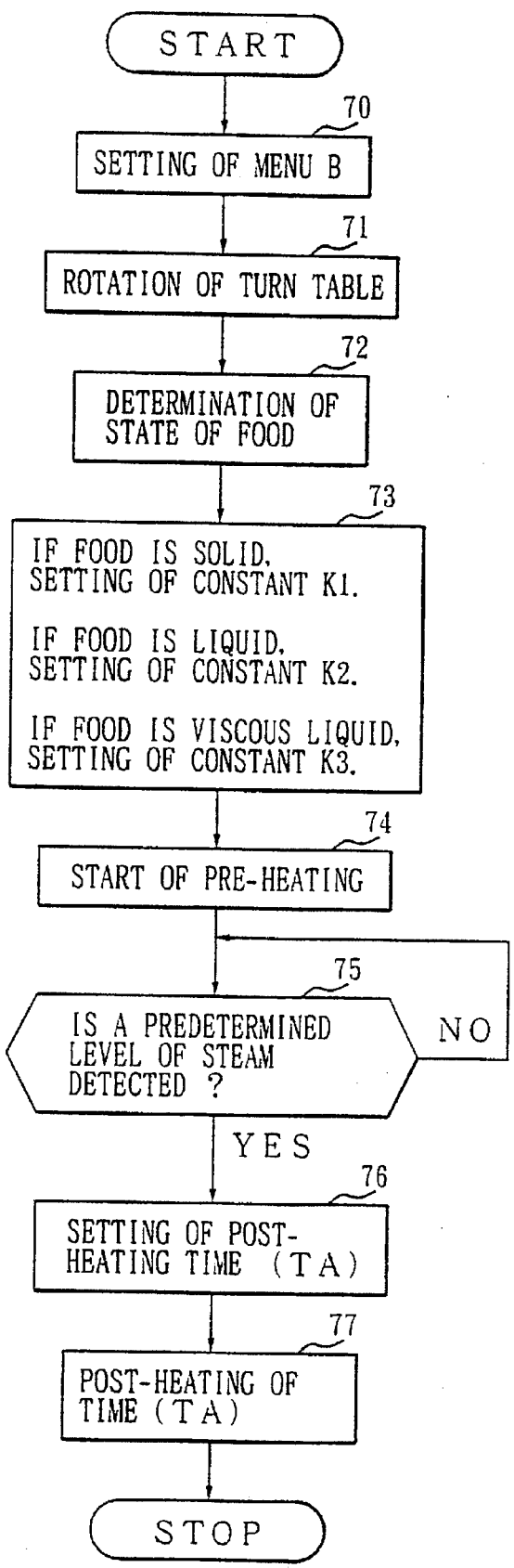
FIG. 15 is a flow chart of the operation of the automatic oven Of the sixth embodiment.

Subsequently, heating operation in the menu B is described hereafter with reference to FIG. 15. The menu B is selected at step 70. The turntable 2 starts rotation at step 71. The state of food is determined at step 72. The detailed process at step 72 is identical with that of step 58 or 64 as shown in FIG. 16. On the basis of the determination result at step 72, when the state is solid at step 71, the constant K1 is selected. Additionally, when the state is liquid, the constant K2 is selected, and when the state is viscous liquid, the constant K3 is selected. These constants K1, K2 and K3 are also used to derive a heating time period TA of the post-heating at step 78. The pre-heating operation is started at step 74. The microwave generator 12A is preferable for heating the food in the menu B in general. After a start of heating operation, steam emanated from the food is detected by the steam sensor 13 at step 75. When the detected value of the steam sensor 13 reaches a predetermined level, the time period TA of the post-heating operation is set at step 76. The post-heating operation is performed for the time period TA at step 77. Then, the heating operation is completed.

Hereafter, the value of the constant K is described in detail. As shown in the table 1, the constant K is predetermined for various kinds of food by experiments. How to decide the constant K is described hereafter. When a food is heated the steam is emanated. The steam is detected by the steam sensor 13. A time length "t" is defined as a time period from start of heating operation to arrival of the detected value of the steam sensor 13 to a predetermined value. The food heated during the time period t is not yet heated to a desired temperature. Therefore, the post-heating operation is further continued. When the temperature of the food reaches the desired temperature, the post-heating Operation is completed. The constant K is derived by a ratio of the time period TA to the time period t (K=TA/t). In the case of the boiled rice, the value of constant K1 is 0.1, for example, the rice reaches a desired temperature by the post-heating operation for one tenth of the time period t of the pre-heating operation. A total heating time Th in this case is 1.1t (Th=(1+0.1)t). In the case of the soup, the constant K2 is 1.7, therefore, length of the time period TA of the post-heating operation is as 1.7 times long as the time period t of the pre-heating operation. Consequently, a total heating time Th is 2.7t (Th=(1+1.7)t).

[Seventh Embodiment]

Figure 17:
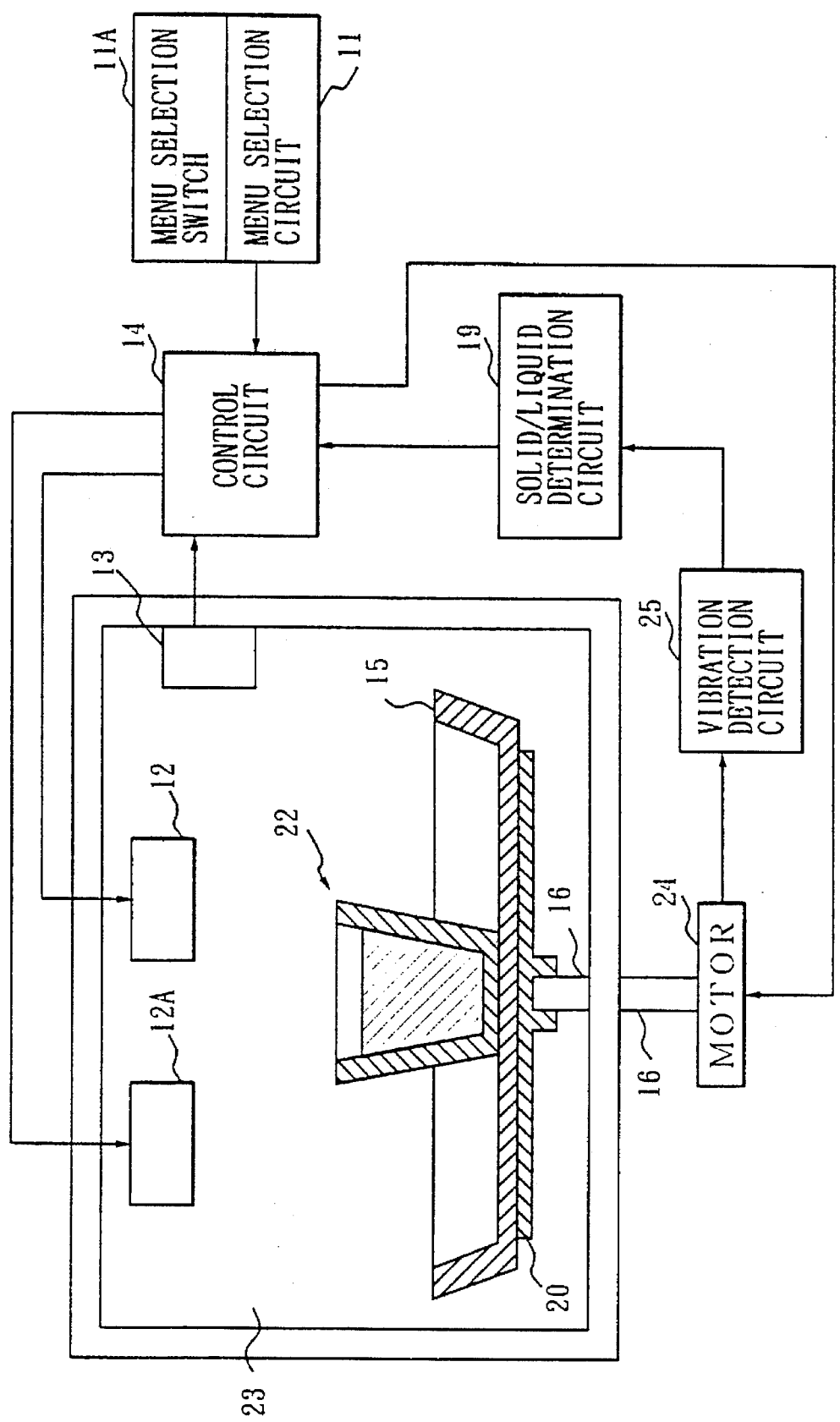
FIG. 17 is a block diagram of the automatic oven of a seventh embodiment using the solid/liquid determination apparatus of the third embodiment.

FIG. 17 is a block diagram of an automatic oven of the seventh embodiment of the present invention. In the seventh embodiment, the turntable 15 is rotated by an induction motor 24, and the solid/liquid determination apparatus is similar to that of the third embodiment shown in FIG. 5. The induction motor 24 outputs a detected signal by vibration of the turntable 15 in a similar manner to the third embodiment. The detected signal is amplified by the vibration detection circuit 25, and is applied to the solid/liquid determination circuit 19. The rest of the configuration and operation are substantially identical with those of the sixth embodiment, and description is omitted.

According to the seventh embodiment, the vibration is detected by the induction motor 24 for rotating the turntable 2, and therefore, there is no need of the vibration sensor 18 under the turntable 2, and hence the structure is simplified.

[Eighth Embodiment]

FIG. 18 is a block diagram of an automatic oven of the eighth embodiment of the present invention. In the eighth embodiment, the vibration of the turntable 15 is detected by a weight detector 10, and a detected output applied to a weight and vibration detection circuit The solid/liquid determination apparatus of the eighth embodiment is substantially identical with that of the fourth embodiment. The output signal of the weight and vibration detection circuit 28 is applied to the solid/liquid determination circuit 19. The heating operation of the eighth embodiment is similar to that of the sixth embodiment, and the detailed description is omitted.

In the eighth embodiment, the weight of a food placed on the turntable 15 is detected by the weight detector 10. The detected signal of the weight detector 10 is applied to the weight and vibration detection circuit 26, and a net weight of the food in the object 22 is derived by subtracting the weights of the turntable 15 and motor 24. The weight of the food is inputted to the control circuit 14, and the output of the electric heater 12 or the microwave generator 12A is controlled on the basis of a predetermined control process. Consequently, according to the eighth embodiment, a heating operation is also controlled in accordance with the weight of the food, and thus the food is heated to an optimum temperature.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A solid/liquid determination apparatus comprising:

a movable table for receiving an object which is in a solid and/or a liquid state, means for driving said movable table, control means for controlling said means for driving said movable table, vibration detection means for detecting an amplitude of vibration of said movable table, and state determination means for determining whether said object is in a solid or liquid state by detecting the amplitude of vibration of said movable table with said vibration detection means immediately after stopping said driving of said movable table, the state of said object being liquid when the amplitude of vibration is equal to or greater than a predetermined value, the state of said object being solid when the amplitude of vibration is less than said predetermined value.

2. A solid/liquid determination apparatus comprising:

a turn table for receiving an object which is in a solid and/or a liquid state, the object being rotated at a predetermined rotation speed by rotation means, vibration detection means for detecting an amplitude of vibration of said turn table, rotation control means for starting rotation of said turn table and stopping rotation after a predetermined time period, and state determination means for determining whether said object is in a solid or a liquid state by detecting the amplitude of vibration of said turn table with said vibration detection means immediately after stopping said rotation of said turn table, the state of said object being liquid when the amplitude of vibration is equal to or greater than a predetermined value, the state of said object being solid when the amplitude of vibration is less than said predetermined value.

3. A solid/liquid determination apparatus in accordance with claim 1, wherein said vibration detection means is a non-contact displacement gauge.

4. A solid/liquid determination apparatus in accordance with claim 2, wherein said rotation means is an induction motor, and the amplitude of vibration of said table is detected by measuring an induction current of said induction motor.

5. A solid/liquid determination apparatus in accordance with claim 1, wherein said vibration detection means is a weight detector coupled to said movable table.

6. A solid/liquid determination apparatus in accordance with claim 2, wherein said rotation control means rotates said table during a first predetermined time period, and subsequently rotates in a reverse direction of rotation during a second predetermined time period and stops the rotation after said second predetermined time period the state determination means detecting the amplitude of vibration immediately after said second predetermined time period.

7. A solid/liquid determination apparatus in accordance with claim 1, wherein said state determination means determines said object to be in a liquid state when the amplitude of vibration of said table is equal to or greater than a first predetermined value, or a solid state when the amplitude of vibration is equal to or less than a second predetermined value, the second predetermined value being smaller than said first predetermined value, or a mixture of liquid and solid state when the amplitude of vibration is between said first predetermined value and said second predetermined value.

8. A solid/liquid determination apparatus in accordance with claim 1, wherein said state determination means determines said object to be liquid when a duration of said vibration of said table is equal to or longer than a predetermined time period and determines said object to be viscous liquid when the duration of said vibration is smaller than said predetermined time period.

9. A solid/liquid determination apparatus in accordance with claim 2, wherein said vibration detection means is a non-contact displacement gauge.

10. A solid/liquid determination apparatus in accordance with claim 2, wherein said vibration detection means is a weight detector coupled to said movable table.

11. A solid/liquid determination apparatus in accordance with claim 2, wherein said state determination means determines said object to be in a liquid state when the amplitude of vibration of said table is equal to or greater than a first predetermined value, or a solid state when the amplitude of vibration is equal to or less than a second predetermined value, the second predetermined value being smaller than said first predetermined value, or a mixture of liquid and solid state when the amplitude of vibration is between said first predetermined value and said second predetermined value.

12. A solid/liquid determination apparatus in accordance with claim 2, wherein said state determination means determines said object to be liquid when a duration of said vibration of said table is equal to or longer than a predetermined time period and determines said object to be viscous liquid when the duration of said vibration is smaller than said predetermined time period.

* * * * *